(12) United States Patent
Moberg et al.

(10) Patent No.: US 6,485,465 B2
(45) Date of Patent: Nov. 26, 2002

(54) METHODS, APPARATUSES, AND USES FOR INFUSION PUMP FLUID PRESSURE AND FORCE DETECTION

(75) Inventors: Sheldon B. Moberg, Granada Hills, CA (US); James D. Causey, III, Simi Valley, CA (US); Rex O. Bare, Lake Forest, CA (US); Andrew J. Scherer, San Dimas, CA (US); Bradley J. Sargent, Mission Viejo, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 09/819,208

(22) Filed: Mar. 27, 2001

(65) Prior Publication Data

US 2001/0034502 A1 Oct. 25, 2001

Related U.S. Application Data

(60) Provisional application No. 60/243,392, filed on Oct. 26, 2000, and provisional application No. 60/192,901, filed on Mar. 29, 2000.

(51) Int. Cl.[7] ............................................. A61M 37/00
(52) U.S. Cl. .......................... 604/154; 604/31; 604/65; 604/67; 604/155; 417/18
(58) Field of Search ............................. 604/30–34, 65, 604/66, 67, 152, 154, 155; 417/18, 474

(56) References Cited

U.S. PATENT DOCUMENTS

| 5,096,385 A | * | 3/1992 | Georgi et al. ............. 604/67 X |
| 5,501,665 A | | 3/1996 | Jhuboo et al. |
| 5,647,853 A | | 7/1997 | Feldman et al. |
| 5,695,473 A | | 12/1997 | Olsen |

FOREIGN PATENT DOCUMENTS

EP 0278146 5/1987

* cited by examiner

*Primary Examiner*—Steven J. Ganey
(74) *Attorney, Agent, or Firm*—Medtronic MiniMed, Inc.

(57) ABSTRACT

An occlusion detection system detects an occlusion in a fluid path of an infusion pump. The infusion pump is for delivering fluid to a user. The infusion pump includes a housing, a motor, a reservoir, one or more drive train components, a sensor, and an electronics system. The motor is contained within the housing. The reservoir contains the fluid to be delivered. The one or more drive train components react to stimulus from the motor to force the fluid from the reservoir into the user. The sensor is positioned to measure a parameter associated with the motor or a drive train component, and the sensor produces three or more output levels across a range of measurements. The electronics system processes the senor output levels to declare when an occlusion exists.

31 Claims, 22 Drawing Sheets

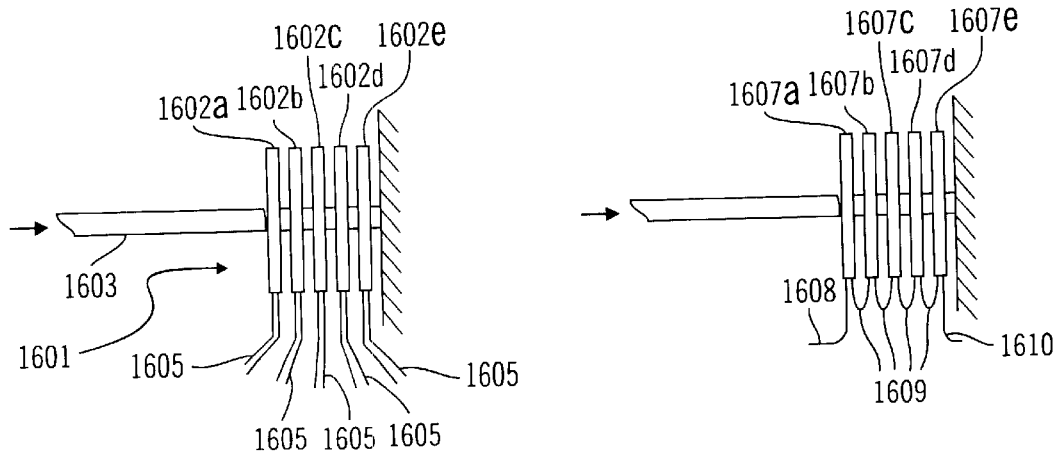
FIG. 14(a)
FIG. 14(b)
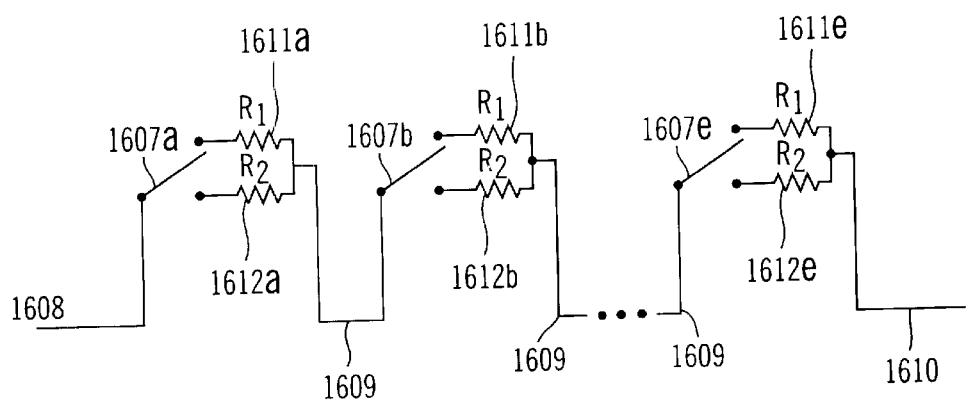
FIG. 14(c)

METHODS, APPARATUSES, AND USES FOR INFUSION PUMP FLUID PRESSURE AND FORCE DETECTION

RELATED APPLICATIONS

This application claims priority from U.S. Provisional Patent Application Serial No. 60/243,392, filed Oct. 26, 2000, entitled, "IMPROVED METHODS AND APPRATUSES FOR DETECTION OF FLUID PRESSURE"; and U.S. Provisional Patent Application Serial No. 60/192,901, filed Mar. 29, 2000, entitled, "PRESSURE SENSING SYSTEM AND METHOD FOR DRUG DELIVERY DEVICES", which are incorporated herein by reference.

FIELD OF THE INVENTION

This invention relates generally to improvements in infusion pumps such as those used for controlled delivery of fluid to a user. More specifically, this invention relates to improved methods and apparatuses for detecting fluid pressure and occlusions in fluid delivery paths of infusion pump systems.

BACKGROUND OF THE INVENTION

Infusion pump devices and systems are relatively well-known in the medical arts, for use in delivering or dispensing a prescribed medication such as insulin to a patient. In one form, such devices comprise a relatively compact pump housing adapted to receive a syringe or reservoir carrying a prescribed medication for administration to the patient through infusion tubing and an associated catheter or infusion set.

A typical infusion pump includes a housing, which encloses a pump drive system, a fluid containment assembly, electronics system, and a power supply. The pump drive system typically includes a small motor (DC, stepper, solenoid, or other varieties) and drive train components such as gears, screws, and levers that convert rotational motor motion to a translational displacement of a stopper in a reservoir. The fluid containment assembly typically includes the reservoir with the stopper, tubing, and a catheter or infusion set to create a fluid path for carrying medication from the reservoir to the body of a user. The electronics system regulates power from the power supply to the motor. The electronics system may include programmable controls to operate the motor continuously or at periodic intervals to obtain a closely controlled and accurate delivery of the medication over an extended period. Such pump drive systems are utilized to administer insulin and other medications, with exemplary pump constructions being shown and described in U.S. Pat. Nos. 4,562,751; 4,678,408; 4,685,903; 5,080,653 and 5,097,122, which are incorporated by reference herein.

Infusion pumps of the general type described above have provided significant advantages and benefits with respect to accurate and timely delivery of medication or other fluids over an extended period compared to manual syringe therapy. The infusion pump can be designed to be extremely compact as well as water resistant, and may be adapted to be carried by the user, for example, by means of a belt clip or a harness. As a result, precise amounts of medication may be automatically delivered to the user without significant restriction on the user's mobility or life-style, including in some cases the ability to participate in water sports.

In the past, medication infusion pump drive systems have included alarm systems designed to detect and indicate a pump malfunction and/or non-delivery of the medication to the patient due to a fluid path occlusion. Such alarm systems have typically used a limit switch to detect when the force applied to the reservoir stopper reaches a set point. One known detector uses an "on/off" limit switch. When a set point is reached, the switch changes state (from open to closed or visa versa) triggering an alarm to warn the user. In U.S. Pat. No. 4,562,751, the limit switch is positioned at one end of a rotatable lead screw. The force applied to the limit switch by the lead screw is proportional to the pressure applied to the medication as a result of power supplied to the drive system to advance the stopper.

When an occlusion develops in the fluid path, the first consequence is the lack of medication delivery, or "under-dosing." But, a potentially much greater danger arises from "over-dosing" due to an occlusion breaking free after pressure has built up in the fluid path. For example, if a drive system continues to receive commands to deliver medication when the fluid path is blocked, fluid pressure may continue to grow until the occlusion is forced out, which then causes a lot or the previously commanded medication to be expelled at once under pressure. This could result in an "over dose." Thus, early detection of an occlusion minimizes the potential for "over-dosing."

However, the use of an on/off limit switch as an occlusion detector has several disadvantages. The lead screw or other drive mechanism generally moves axially some distance to actuate the limit switch. If the medication is highly concentrated, and small incremental deliveries are required, such as 0.5 micro liters, then the required stopper displacement per delivery is very small. When an occlusion develops, the lead screw displacement toward the limit switch is also small. Therefore, many deliveries may be missed before the lead screw is displaced sufficiently to actuate the limit switch.

Additionally, a limit switch typically has only one set point. Noise, temporary pressure fluctuations during a delivery, and temperature and/or humidity effects may trigger false occlusion alarms. If the set point were placed higher to avoid some of the false detections, additional time would be required to detect a genuine occlusion.

SUMMARY OF THE DISCLOSURE

According to an embodiment of the invention, an occlusion detection system for detecting an occlusion in a fluid path of an infusion pump with a reservoir containing fluid for delivering fluid to a user includes a housing, a motor, a reservoir, one or more drive train components, a sensor, and an electronics system. The motor is contained within the housing, and the one or more drive train components react to stimulus from the motor to force fluid from a reservoir into the user. The sensor is positioned to measure a parameter associated with the motor or a drive train component, and the sensor produces three or more output levels across a range of measurements. The electronics system processes the three or more sensor output levels to declare when an occlusion exists.

In preferred embodiments, the sensor measures a force proportional to a force applied to a drive train component. In particular embodiments, the drive train component is a lead screw. In other particular embodiments, the drive train component is a slide.

In alternative embodiments, the sensor measures tension or compression on a beam proportional to a torque applied to the motor. In particular embodiments, the drive train component is a beam. In other particular embodiments, the drive train component is one or more mounts.

In other alternative embodiments, the sensor measures tension or compression proportional to a pressure applied to a drive train component. In particular embodiments, the drive train component is a bellows. In other particular embodiments the drive train component is a cap.

In preferred embodiments, the sensor is a force sensitive resistor. In alternative embodiments, the sensor is a capacitive sensor. In other alternative embodiments, the sensor is a strain gauge. In still other alternative embodiments the sensor is a piezoelectric sensor.

In preferred embodiments, the electronics system uses a maximum measurement threshold method to declare when an occlusion exists. In particular embodiments, a measurement threshold is at least 2.00 pounds.

In alternative embodiments, the electronics system uses a slope threshold method to declare when an occlusion exists. In particular embodiments, a slope threshold is about 0.05 pounds per measurement.

In other alternative embodiments, the electronics system uses a maximum measurement threshold method, and a slope threshold method to declare when an occlusion exists. In still other alternative embodiments, one or more measurements must exceed a minimum level to declare that an occlusion exists.

In preferred embodiments, the measured parameter is correlated with a fluid pressure in the reservoir. In particular embodiments, the electronics system processes the sensor output levels to determine when the reservoir is empty. In other particular embodiments, the electronics system processes the sensor output levels to determine when a stopper contacts an end of the reservoir. In still other particular embodiments, the electronics system processes the sensor output levels to determine when a slide is seated in a stopper.

In preferred embodiments, the sensor is positioned between the motor and a housing component. In particular embodiments, VHB adhesive is positioned between the motor and the housing component. In other particular embodiments, one or more components including the sensor are stacked between the motor and the housing component, and the housing component is positioned to remove space between the one or more components before the housing component is attached to the housing. In alternative embodiments, one or more components including the sensor are stacked between the motor and the housing, and back-fill material is injected through the housing to remove space between the one or more components and to fill the space between the one or more components and the housing.

According to an embodiment of the invention, a method of detecting an occlusion in an infusion pump for infusing fluid into the body of a user includes the steps of obtaining a measurement from a sensor before each fluid delivery, calculating a slope of a line generated using two or more measurements, comparing the slope to a slope threshold, incrementing a counter when the slope exceeds the slope threshold, and declaring an occlusion when the counter exceeds a detection count According to another embodiment of the invention, a method of detecting an occlusion in an infusion pump for infusing fluid into the body of a user includes the steps of obtaining a measurement from a sensor before each fluid delivery, calculating a current slope of a line using two or more measurements, calculating an average slope using a previous average slope and the current slope, comparing the average slope to a slope threshold, incrementing a counter when the average slope exceeds the slope threshold, and declaring an occlusion when the counter exceeds a detection count value. In preferred embodiments, the two or more measurements are not consecutive.

According to another embodiment of the invention, an occlusion detection system for detecting an occlusion in a fluid path of an infusion pump with a reservoir containing fluid for delivering fluid to a user includes, a housing, forcing means for forcing fluid from a reservoir containing a fluid, sensing means for sensing a parameter associated with the forcing means for forcing fluid from the reservoir containing the fluid to obtain one or more measurements, and evaluation means. The sensing means producing one of three or more output levels for each of the one or more the measurements. The evaluation means evaluates the one of three or more output levels associated with each of the one or more measurements to declare when an occlusion exists.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

FIG. 6(*b*) is a cross-sectional view of a force sensitive resistor style sensor according to a fourth embodiment of the present invention.

FIG. 7(*b*) is an exploded top/front perspective view of the infusion pump drive system, sensing system, and fluid containing assembly of FIG. 7(*a*).

FIG. 7(*c*) is a cross-sectional side view of an assembled infusion pump drive system, sensing system, and fluid containing assembly of FIG. 7(*b*).

FIG. 7(*d*) is an enlarged cross-sectional side view of the sensing system shown as 7 (*d*) in FIG. 7(*c*).

FIG. 8(*b*) is a side view of the disk of the sensing system of FIGS. 7(*a*)–(*d*).

FIG. 8(*c*) is a bottom view of the disk of the sensing system of FIGS. 7(*a*)–(*d*).

FIG. 14(a) is a side plan view of a multi-switch sensor, where the switches are mounted in series and are individually electrically monitored according to an eighth embodiment of the present invention.

FIG. 14(b) is a side plan view of a multi-switch sensor, where the switches are mounted in series and are electrically connected in series according to a ninth embodiment of the present invention.

FIG. 14(c) is an electrical schematic for a multi-switch sensor, where the switches are electrically connected in series according to a tenth embodiment of the present invention.

DETAILED DESCRIPTION OF THE PREFERRED EMBODIMENTS

Figure 1:
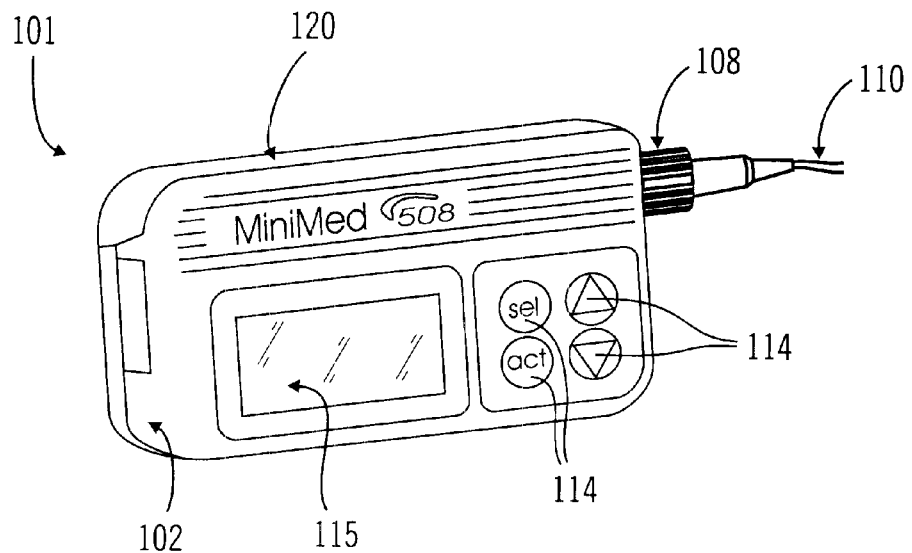
FIG. 1 is a front, perspective view of an infusion pump, according to an embodiment of the present invention.

As shown in the drawings for purposes of illustration, the invention is embodied in a pressure sensing system for an infusion pump. The infusion pump is used for infusing fluid into the body of a user. In preferred embodiments, the infused fluid is insulin. In alternative embodiments, many other fluids may be administered through infusion such as, but not limited to, HIV drugs, drugs to treat pulmonary hypertension, iron chelation drugs, pain medications, anti-cancer treatments, medications, vitamins, hormones, or the like.

In preferred embodiments, a programmable controller regulates power from a power supply to a motor. The motor actuates a drive train to displace a slide coupled with a stopper inside a fluid filled reservoir. The slide forces the fluid from the reservoir, along a fluid path (including tubing and an infusion set), and into the user's body. In preferred embodiments, the pressure sensing system is used to detect occlusions in the fluid path that slow, prevent, or otherwise degrade fluid delivery from the reservoir to the user's body. In alternative embodiments, the pressure sensing system is used to detect when: the reservoir is empty, the slide is properly seated with the stopper, a fluid dose has been delivered, the infusion pump is subjected to shock or vibration, the infusion device requires maintenance, or the like. In further alternative embodiments, the reservoir may be a syringe, a vial, a cartridge, a bag, or the like.

In general, when an occlusion develops within the fluid path, the fluid pressure increases due to force applied on the fluid by the motor and drive train. As power is provided to urge the slide further into the reservoir, the fluid pressure in the reservoir grows. In fact, the load on the entire drive train increases as force is transferred from the motor to the slide, and the slide is constrained from movement by the stopper pressing against the fluid. An appropriately positioned sensor can measure variations in the force applied to one or more of the components within the drive train. The sensor provides at least three output levels so measurements can be used to detect an occlusion and warn the user.

Early occlusion detection minimizes the time the user is without medication and more importantly, minimizes the potential of overdosing caused when an occlusion breaks free and fluid rushes into the user's body to relieve the built up pressure from the reservoir. In preferred embodiments, an occlusion is detected before the pressure is high enough to deliver a dose greater than a maximum allowable bolus. Generally, the maximum allowable bolus is the maximum amount of fluid that may be delivered safely into the user at one time, which depends on the concentration of ingredients in the fluid, the sensitivity of the user to the fluid, the amount of fluid that the user presently needs, the amount of fluid still available in the user from previous deliveries, or the like. The pressure in the reservoir, or the force on the drive train components, associated with the maximum allowable bolus depends on the diameter of the reservoir, leverage in the drive train, friction, and the like.

Figure 2:
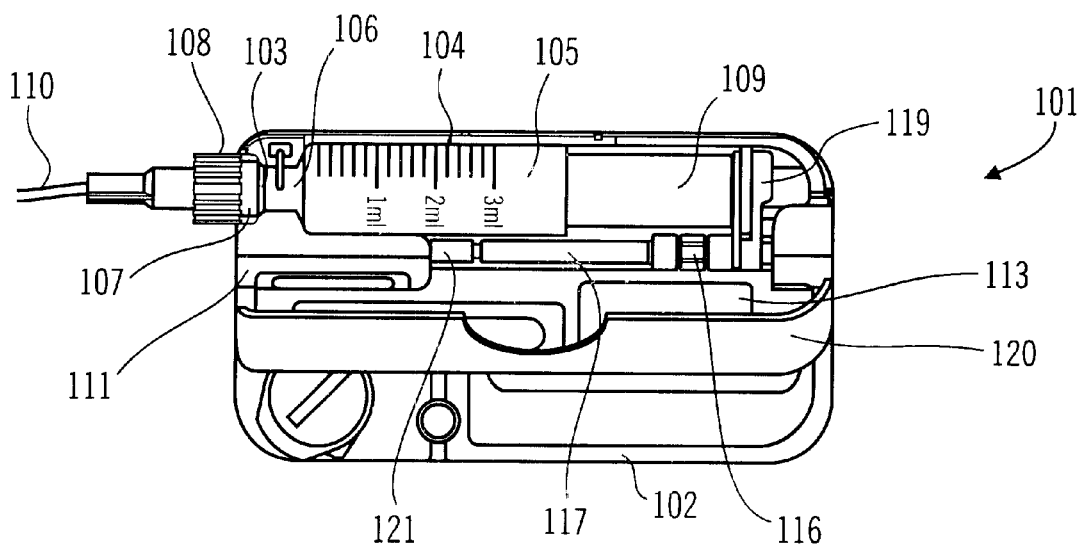
FIG. 2 is a rear view of the infusion pump of FIG. 1, with a rear door open to illustrate particular internal components.
Figure 3:
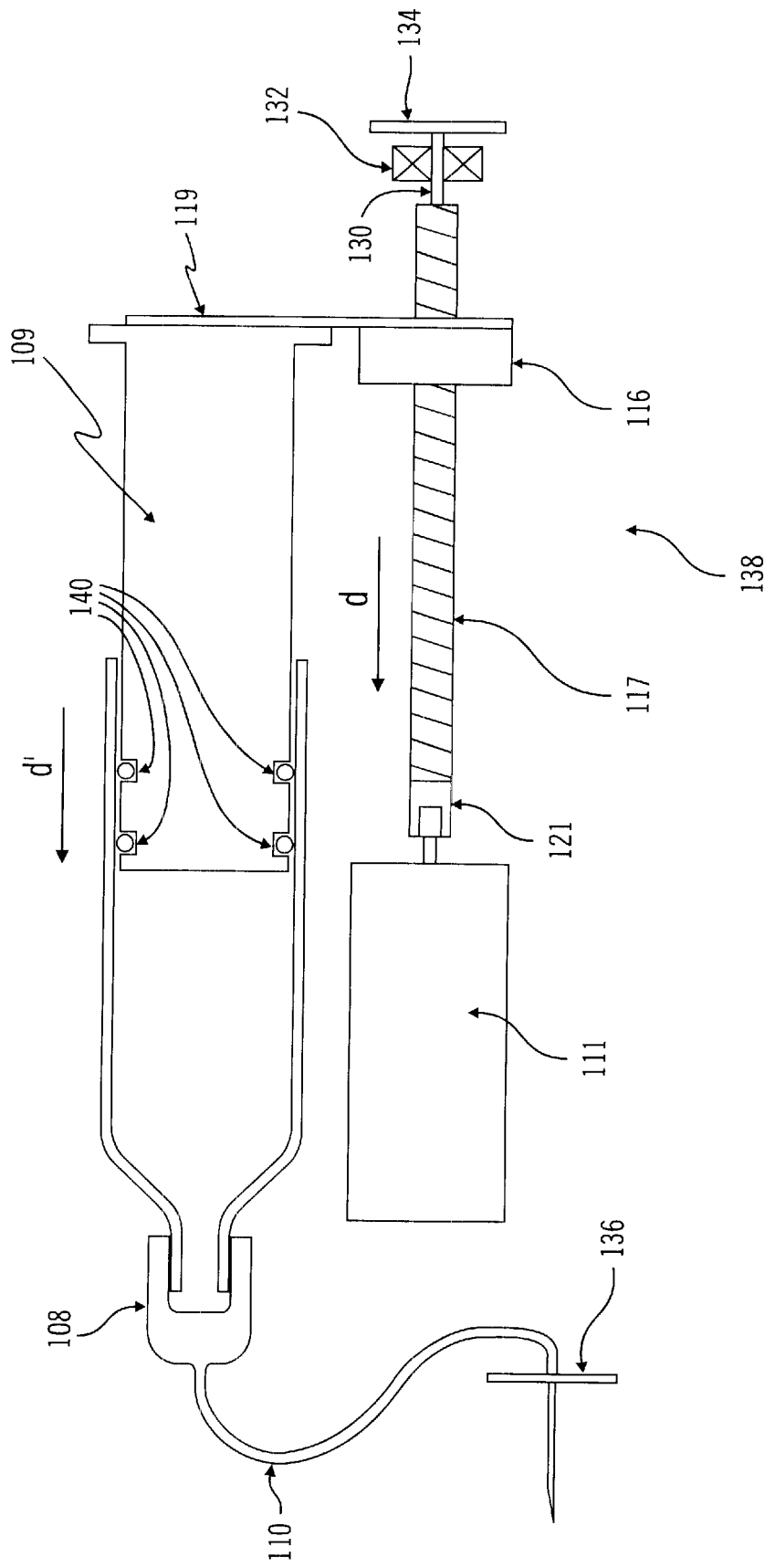
FIG. 3 is an illustration view of a drive system of the infusion pump of FIG. 1.

In preferred embodiments, as shown in FIGS. 1–3, an infusion pump 101 includes a reservoir 104, a slide 109, a drive system 138, a programmable controller 113, and a power supply (not shown), all contained within a housing 102. The housing 102 has a rear door 120, which may be pivoted open to provide access to the interior of the pump 101 for removing and replacing the reservoir 104 and the slide 109 (FIG. 2 shows the rear door 120 pivoted to an open position).

The fluid-containing reservoir 104 includes a reservoir barrel 105, a neck 106, and a head 103, which are generally concentrically aligned. The neck 106, which has a smaller diameter than the barrel 105, connects a front end of the barrel 105 to the head 103. The neck 106 seats within an outlet port 107 formed in the housing 102. The head 103, which has a larger diameter than the neck 106, extends through the housing 102. The head 103 mates with tubing 110 by means of a fitting 108, thereby establishing fluid communication from the barrel 105, through the housing 102, and into the tubing 110. The tubing 110 extends from the fitting 108 to an infusion set 136, which provides fluid communication with the body of the user. A rear end of the barrel 105 forms an opening to receive the slide 109. Fluid is forced from the reservoir 104 as the drive system 138 moves the slide 109 from the rear end of the barrel 105 toward the front end of the barrel 105.

The drive system 138, best shown in FIG. 3, includes a motor 111, a coupler 121, a lead screw 117, a drive nut 116, and one or more latch arms 119. The motor 111 is coupled to the lead screw 117 by the coupler 121. The motor rotates the coupler 121, which in turn rotates the lead screw 117. The drive nut 116 includes a bore with internal threads (not shown). External threads on the lead screw 117 mesh with the internal threads on the drive nut 116. As the lead screw 117 rotates in response to the motor 111, the drive nut 116 is forced to travel along the length of the lead screw 117 in an axial direction d. The one or more latch arms 119 are attached to the drive nut 116, and extend away from the drive nut 116 to engage the slide 109, thereby coupling the slide 109 to the drive nut 116. Thus, as the drive nut 116 is forced to translate along the length of the lead screw 117 in axial direction d, the slide 109 is forced to translate parallel to the lead screw 117 in an axial direction d'.

Power is supplied to the motor 111 by the power supply (not shown), in response to commands from the programmable controller 113. Preferably, the motor 111 is a solenoid motor. Alternatively, the motor may be a DC motor, AC motor, stepper motor, piezoelectric caterpillar drive, shape memory actuator drive, electrochemical gas cell, thermally driven gas cell, bimetallic actuator, or the like. In alternative embodiments, the drive train includes one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. Preferably, the power supply is one or more batteries. Alternatively, the power supply may be a solar panel, capacitor, AC or DC power supplied through a power cord, or the like.

The programmable controller 113 may be programmed by a care provider such as a physician or trained medical personnel, or by the user. In preferred embodiments, programming is conducted using an array of buttons 114 and a display 115 located on a face of the housing 102. The display 115 provides information regarding program parameters, delivery profiles, pump operation, alarms, warnings, statuses, or the like. In preferred embodiments, the programmable controller 113 operates the motor 111 in a stepwise manner, typically on an intermittent basis; to administer discrete precise doses of the fluid to the user according to programmed delivery profiles. In alternative embodiments, the programmable controller operates the motor continuously.

In preferred embodiments of the present invention, the lead screw 117 includes a support pin 130 that extends through one or more bearings 132 and maintains contact with a sensor 134 positioned to detect forces applied by the lead screw 117 along the axis of the lead screw 117. The one or more bearings 132 and the coupler 121 are designed to allow the lead screw some translational freedom of movement along its axis while providing lateral support. The sensor 134 is therefore subjected to all axial forces applied to the lead screw 117 in the direction away from the motor 111. The axial force exerted by the lead screw 117 on the sensor 134 is generally correlated with the fluid pressure in the reservoir 109. For example, if an occlusion developed within the fluid path, blocking fluid delivery from the infusion pump to the body of the user, the fluid pressure would increase as the slide 109 is forced forward by the drive system 138. Each time the programmable controller 113 commands power to be supplied to the motor 111, the slide 109 is driven forward into the reservoir 104, therefore increasing the fluid pressure. The fluid pressure is partially relieved by compliance in the system, for example, expansion of the tubing 110 and the reservoir 109, deformation of one or more O-ring seals 140 on the slide 109, or the like. The remaining pressure is exerted against the slide 109, forcing it to back out of the reservoir 104. But the slide 109 is prevented from moving by the one or more latch arms 119. The latch arms 119 transfer the force from the slide 109 to the drive nut 116, which in turn transfers the force, by way of thread engagement, to the lead screw 117. The sensor 134 is then subjected to a force with a magnitude correlated with the fluid pressure. Preferably, the sensor 134 provides at least three output levels across the magnitude of sensed forces. An electronics system (not shown) supports the sensor 134 by providing power and/or signal processing, depending on the type of sensor 134.

Figure 4:
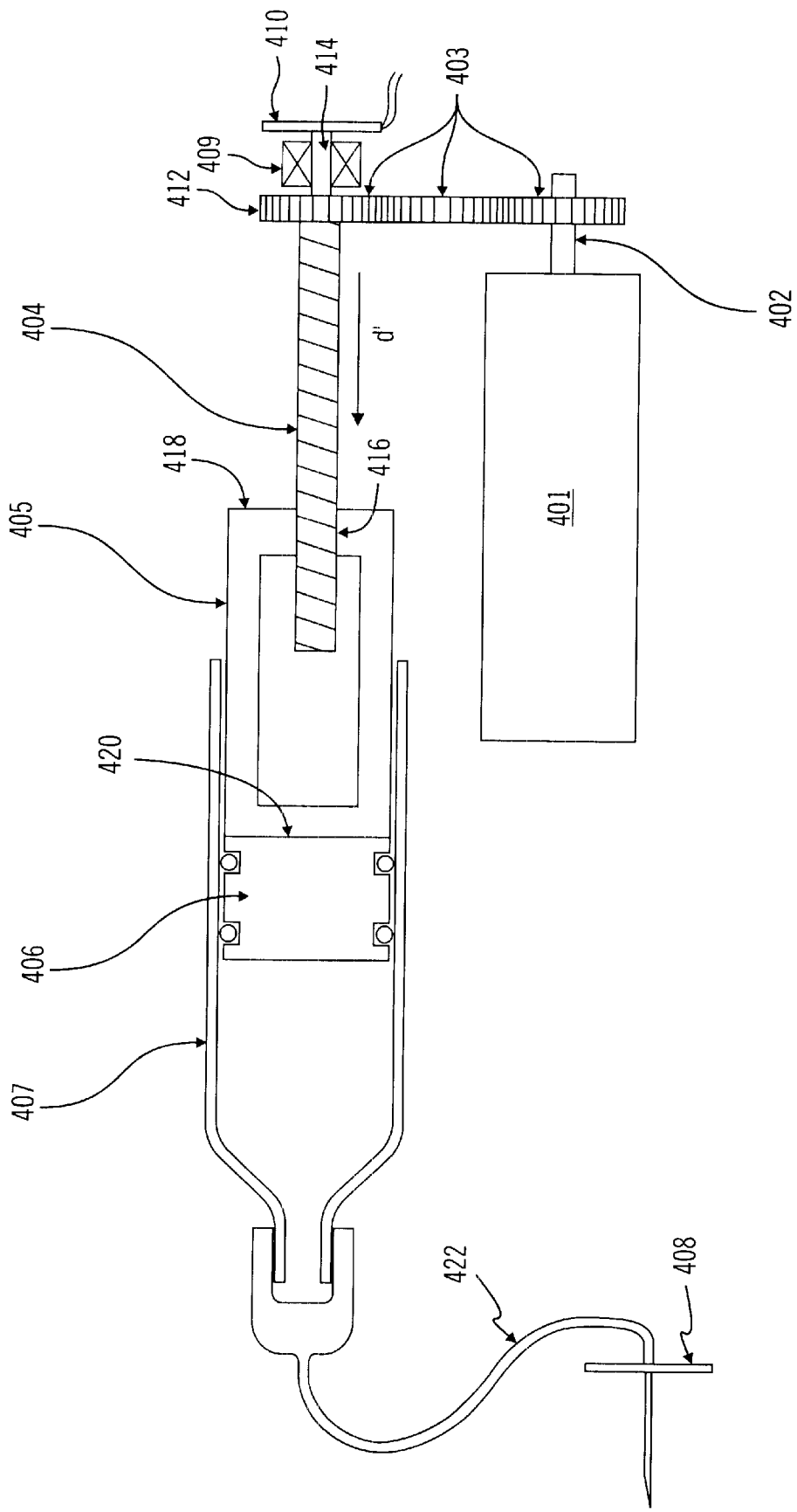
FIG. 4 is an illustration view of an infusion pump drive system with a sensor according to a second embodiment of the present invention.

In alternative embodiments, a motor 401 (or a motor with an attached gear box) includes a drive shaft 402, which drives a set of gears 403, as shown in FIG. 4. A lead screw 404 concentrically aligned with a gear 412 in the set of gears 403 is coupled to rotate with the gear 412. A hollow slide 405 includes an internally threaded bore 416 that passes through a rear end 418 of the slide 405, and engages with external threads of the lead screw 404. The axis of the slide 405 is generally parallel to the axis of the lead screw 404. The slide 405 further includes a tab (not shown) that engages a groove (not shown) in a housing (not shown) that runs parallel to the lead screw 404 to prevent the slide 405 from rotating when the lead screw 404 rotates. Thus, as the lead screw 404 rotates, the slide 405 is forced to translate along the length of the lead screw 404. A front end 420 of the slide 405 engages a stopper 406 inside a reservoir 407. As the slide 405 advances due to the rotation of the lead screw 404, the stopper 406 is forced farther into the reservoir 407, thus forcing fluid from the reservoir 407, through tubing 422, and through an infusion set 408. In alternative embodiments, the stopper and slide are formed as one piece.

The lead screw 404 includes a support pin 414 that extends axially from an end of the lead screw 404 that is not enclosed within the slide 405. The support pin 414 passes through a bearing 409, and maintains contact with a sensor 410. The bearing 409 provides lateral support, and allows the lead screw 404 to have some axial translational displacement. However, the sensor 410 is positioned to prevent the lead screw 404 from translational motion away from the reservoir 407. And therefore, the sensor 410 is positioned to sense forces applied to the lead screw 404 in reaction to fluid pressure within the reservoir 407. The sensor provides at least three output levels based on the measurement of the sensed forces.

Figure 5:
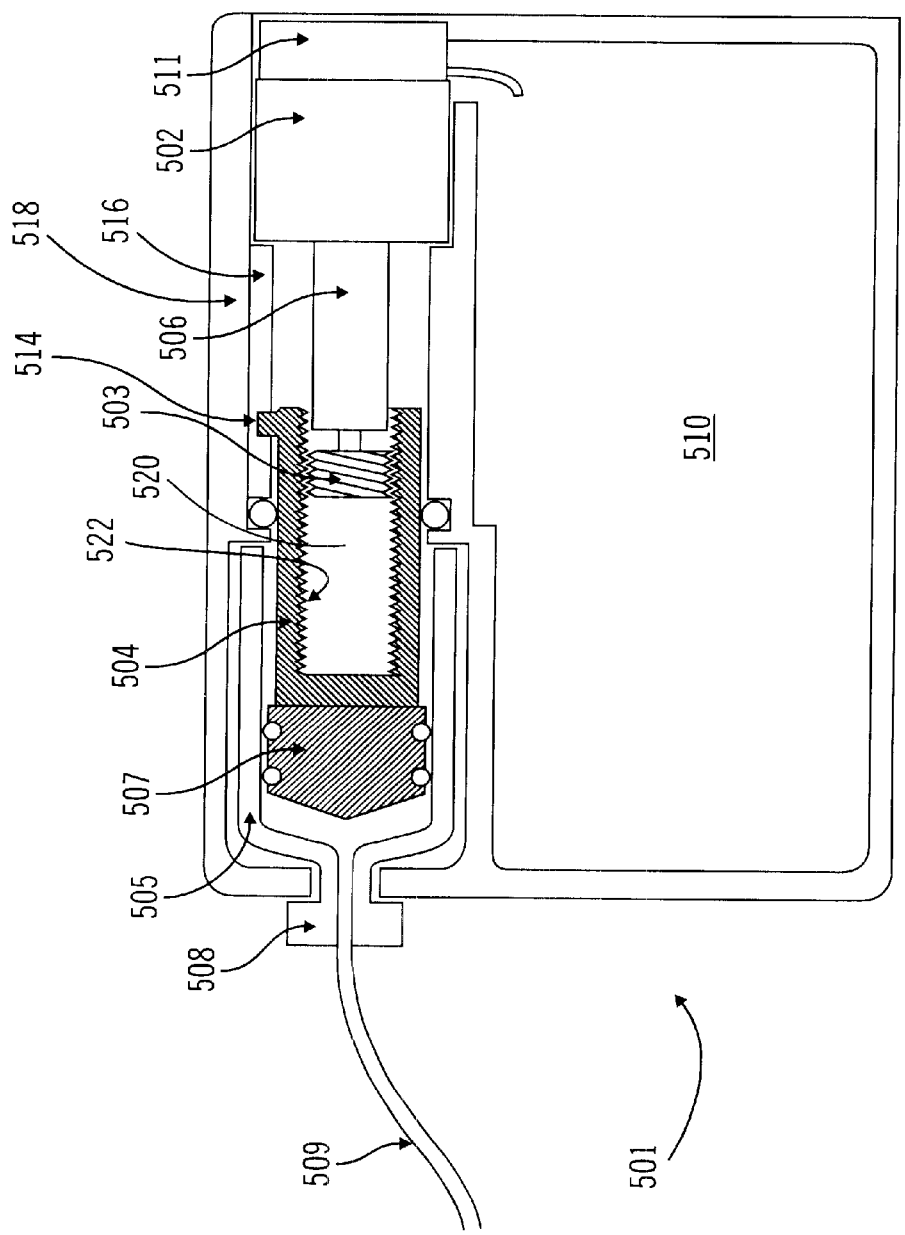
FIG. 5 is an illustration view of an infusion pump drive system with a sensor according to a third embodiment of the present invention.

In other alternative embodiments, an infusion pump 501 includes a motor 502, gear box 506, drive screw 503, slide 504, stopper 507, and a reservoir 505 generally aligned with each other to share a generally common concentric centerline, as shown in FIG. 5. The motor 502 rotates the drive screw 503 via a gear box 506. The drive screw 503 has external threads, which engage internal threads 522 on a cylindrical bore 520 running most of the length of the slide 504. The slide 504 further includes one or more tabs 514 that fit within one or more slots 516 in a housing 518 to prevent the slide 504 from rotating with respect to the housing 518. As the drive screw 503 rotates, the slide 504 is forced to travel along its axis. The slide 504 is in removable contact with a stopper 507 within the reservoir 505. And, as the slide 504 advances into the reservoir 505, the stopper 507 is displaced forcing fluid out of the reservoir 505, through a fitting 508, through tubing 509, and through an infusion set (not shown). A sensor 511 is positioned between the motor 502 in the housing 518 to detect forces translated from fluid pressure within the reservoir 505 through, the stopper 507, slide 504, drive screw 503, and the gear box 506 to the motor 502. The sensor 511 provides at least three output levels based on the detected forces. Further alternative embodiments are described in detail in co-pending application Ser. No. 09/429,352, filed Oct. 28, 1999, which is incorporated by reference herein.

In preferred embodiments, a sensor is a force sensitive resistor, whose resistance changes as the force applied to the sensor changes. In alternative embodiments, the sensor is a capacitive sensor, piezoresistive sensor, piezoelectric sensor, magnetic sensor, optical sensor, potentiometer, micromachined sensor, linear transducer, encoder, strain gauge, and the like, which are capable of measuring compression, shear, tension, displacement, distance, rotation, torque, force, pressure, or the like. In preferred embodiments, the sensor is capable of providing an output signal in response to a physical parameter to be measured. And the range and resolution of the sensor output signal provides for at least three levels of output (three different states, values, quantities, signals, magnitudes, frequencies, steps, or the like) across the range of measurement. For example, the sensor might generate a low or zero value when the measured parameter is at a minimum level, a high or maximum value when the measured parameter is at a relatively high level, and a medium value between the low value and the high value when the measured parameter is between the minimum and relatively high levels. In preferred embodiments, the sensor provides more than three output levels, and provides a signal that corresponds to each change in resistance in a sampled, continuous, or near continuous manner. The sensor is distinguished from a switch, which has only two output values, and therefore can only indicate two levels of output such as, 'on' and 'off,' or 'high' and 'low.'

Preferred embodiments of the present invention employ a force sensitive resistor as the sensor, which changes resistance as the force applied to the sensor changes. The electronics system maintains a constant supply voltage across the sensor. The output signal from the sensor is a signal current that passes through a resistive material of the sensor. Since the sensor resistance varies with force, and the supply voltage across the sensor is constant, the signal current varies with force. The signal current is converted to a signal voltage by the electronics system. The signal voltage is used as a measurement of force applied to a drive train component or fluid pressure in the reservoir. In alternative embodiments, a constant supply current is used and the signal voltage across the sensor varies with force (fluid pressure). In further alternative embodiments, other electronics systems and/or other sensors are used to convert fluid pressure or forces into a measurement used by the electronics system to detect occlusions in the fluid path.

Figure 6A:
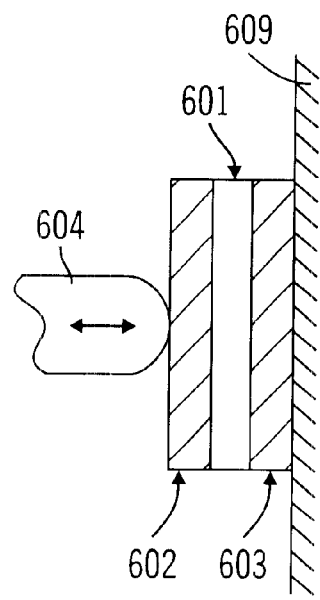
FIG. 6(*a*) is a cross-sectional view of a sensor mounted between a drive system component and a housing according to a first and second embodiment of the present invention as shown in FIGS. 3 and 4.
Figure 6B:
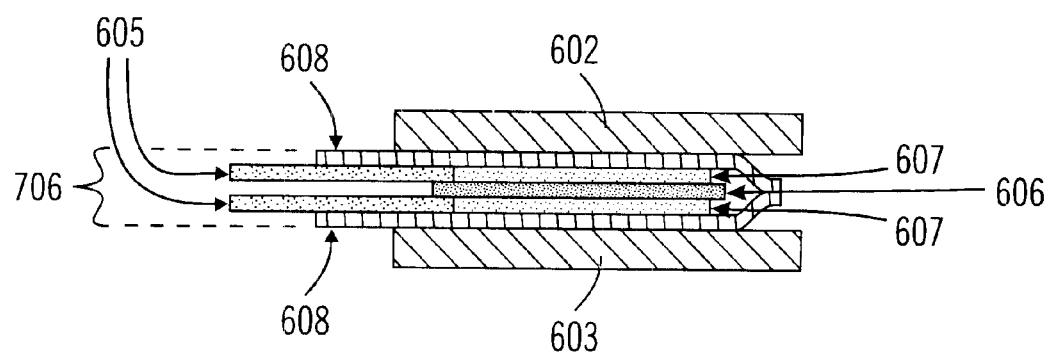

In preferred embodiments, the force resistive sensor 706 has a substantially planar shape and is generally constructed of a layer of force resistive material 606 sandwiched between two conductive pads 607, which are sandwiched within protective outer layers 608, as shown in FIG. 6(b). Electrical leads 605 carry a sensor signal from the conductive pads 607 to the electronics system (not shown). In particular embodiments, the force resistive material layer 606 is a suspension of conductive material in a polymer matrix. The conductive pads 607 and electrical leads 605 are formed from one or more layers of conductive ink, such as silver ink, gold ink, platinum ink, copper ink, conductive polymers, doped polymers, or the like. And the protective outer layers 608 are polyester, which provide electrical insulation as well as protection from the elements. A sensor 706 of the type shown in FIG. 6(b) may be obtained under part number A101, from Tekscan Co. of South Boston, Mass. In alternative embodiments, the protective outer layers are made of other insulating materials such as Mylar, saran, urethane, resins, PVC, plastic, linen, cloth, glass, and the like. In other alternative embodiments, the conductive pads and/or leads are sheets of conductive material, wires, foil, or the like.

In preferred embodiments, the sensor 706 is positioned between flat rigid components to spread the force applied to the sensor 706 across the entire sensor surface area. Preferably, the sensor 706 is located between two flat substantially rigid members, such as a housing and a motor.

In alternative embodiments, a sensor 601 is disposed between a rigid load plate 602 and a rigid back support 603, as shown in FIG. 6(a). The load plate 602 is in contact with an end of a lead screw 604. Examples of embodiments that use a lead screw to supply force to a sensor are shown in FIGS. 3 and 4. The back support 603 is generally secured in place by the pump housing 609. Alternatively, a back support is not needed and the sensor is placed against the pump housing. In other alternative embodiments, the load plate is in contact with the motor or another drive train component. In further alternative embodiments, a layer of adhesive (not shown) is placed between the sensor and a plate or component. In further alternative embodiments, force is applied to only a portion of the sensor.

In preferred embodiments, the design and method for mounting the sensor must: sufficiently limit unintended movement of the slide with respect to the reservoir; minimize space between components; be rigid enough for the sensor to immediately detect small changes in force; avoid preloading the sensor to the point that the sensor range is insufficient for occlusion, seating, and priming detection; provide sufficient resolution for early occlusion detection; compensate for sensor system and drive train component dimensional tolerance stack-up; allow sufficient movement in components of the drive system to compensate for misalignments, eccentricities, dimensional inconsistencies, or the like; avoid adding unnecessary friction that might increase the power required to run the drive system; and protect the sensor from shock and vibration damage.

Generally, once the infusion set is primed and inserted into the user's body, the slide must not be permitted to move in or out of the reservoir unless driven by the motor. If the motor and/or drive train components are assembled in a loose configuration that allows the slide to move within the reservoir without motor actuation, then if the infusion pump is jolted or bumped, fluid could be inadvertently delivered. Consequently, the sensor and/or components associated with mounting the sensor are generally positioned snugly against the drive train component from which force is being sensed, thus preventing the drive train component from moving when the infusion pump is subjected to shock or vibration.

In preferred embodiments, the sensor is positioned so that as soon as the pump motor is loaded during operation, a drive train component applies a load to the sensor. Minimizing space between the sensor and the load-applying drive train component improves the sensor's sensitivity to load fluctuations. Small changes in load may be used to detect trends, and therefore provide an early warning that a blockage is developing before the fluid delivery is stopped entirely.

In preferred embodiments, the sensor and associated electronics are intended to measure forces between 0.5 pounds (0.23 kg) and 5.0 (2.3 kg) pounds with the desired resolution of less than or equal to 0.05 pounds. Yet, the infusion pump including the sensor should survive shock levels that result in much higher forces being applied to the sensor than the intended sensor measurement range. In alternative embodiments, the sensor range is from zero to 10 pounds (4.5 kg). In other alternative embodiments, the sensor range and/or resolution may be greater or smaller depending upon the concentration of the fluid being delivered, the diameter of the reservoir, the force required to operate the drive train, the level of sensor noise, the algorithms applied to detect trends from sensor measurements, or the like.

In preferred embodiments, to compensate for tolerance stack-up, the housing includes a variably positioned housing component that may be variably positioned with respect to a housing body. In particular embodiments, the variably positioned housing component is pressed against the sensor and/or sensor mounting components to remove gaps between the sensor, sensor mounting components and drive components before the variably positioned housing component is assembled with the housing body. Thus, the tolerance stack up between components is removed by adjusting the volume within the housing during assembly.

In alternative embodiments, one or more compressible components are used to compensate for tolerance stack up. In further alternative embodiments, flowable materials such as foam, adhesive, filler, liquid metal, plastic, microbeads, or the like are poured, injected, sprayed, forced, pumped, or the like, into the housing to substantially reduce space between the housing, sensor, sensor mounting components, and/or drive components.

In preferred embodiments, the infusion pump 701 includes a housing 702, and a housing bottom 703 to enclose a drive system 730, a sensing system 740, and a fluid containing assembly 750 as shown in FIGS. 7(a)–(d). The drive system 730 includes a motor assembly 705, a drive-screw 710, and a slide 711. The sensing system 740 includes a sensor 706, an adhesive pad 707, a support disk 708, a housing cap 712, and an optional label 724. And the fluid containing assembly 750 includes a stopper 714, a reservoir 715, and a reservoir connector 716.

The drive system 730 forces fluid out of the reservoir 715 in a controlled and measured manner. The drive-screw 710 mates with threads 717 internal to the slide 711. One or more tangs 718 on the slide 711 ride inside groves 726 in the housing 702 that prevent the slide 711 from rotating. The motor assembly includes a tang 721 that prevents the motor assembly 705 from rotating within the housing 702. Thus, when the motor assembly 705 is powered, the drive screw 710 rotates, and the slide 711 is forced to translate along its axis. A threaded tip 712 on the slide 711 is detachably engaged with internal threads 713 on the stopper 714, as described in detail in co-pending application Ser. No. 09/429,352, filed Oct. 28, 1999, which is incorporated by reference herein. The stopper 714 is positioned to push fluid from inside the reservoir 715 through the reservoir connector 716 into tubing (not shown). The reservoir connector 716 seals the reservoir 715 in the housing 702.

When the motor assembly 705 is inserted into the housing 702, a shoulder 719 on the motor assembly 705 rests against a lip 720 formed on the inside of the housing 702. The lip 720 prevents the motor assembly 705 from translating along its axis in the forward direction (toward the reservoir 715).

The components of the sensing system 740 are stacked behind the motor assembly 705, trapping the sensor 706 between the motor assembly 705 and components that are held in place by the housing bottom 703. Once the housing bottom 703 is securely attached to the housing 702, and the sensor system 740 is in place, the sensor 706 is subjected to axial forces placed on the motor assembly 705 by components of the drive system due to fluid pressure within the reservoir 715.

In preferred embodiments, during the assembly process, care is taken to secure the motor assembly 705 against the lip 720, and essentially eliminate space between components of the sensor system that might allow the motor assembly 705 to move away from the lip 720. Not attaching the motor assembly 705 directly to the lip 720 of the housing 702 allows the motor assembly 705 to pitch and yaw slightly as it operates, and allows the sensor 706 to be subjected to axial forces applied to the motor assembly 705.

In particular embodiments, the slide 711 is threaded onto the drive screw 710, then the motor assembly 705 and slide 711 are slid into the housing 702. The sensor 706 is then positioned on the motor assembly 705. Next, the housing bottom 703 is securely welded to the housing 702. In alternative embodiments, the housing bottom 703 is permanently attached to the housing 702 using one or more adhesives, ultrasonic welding, heat bonding, melting, snap fit, or the like. Once the housing bottom 703 is attached to the housing 702, the remaining components of the sensor system 740 are installed through a hole 704 formed in the housing bottom 703. An adhesive pad 707 is placed on the sensor 706, followed by a rigid disk 708.

In preferred embodiments, the adhesive pad 707 serves several purposes aside from securing the disk 708 to the sensor 706. The adhesive pad 707 material conforms to the surface to correct for surface irregularities on the disk 708 and spread loads evenly across the sensor 706. Furthermore, the adhesive pad 707 has other properties such as a low shear strength that allows the motor assembly 705 some freedom to pitch and yaw, provides shock absorption and/or vibration dampening, and does not substantially compress under the range of forces to be measured by the sensor 706. In particular embodiments, the adhesive pad 707 is a 0.010-inch thick layer of very high bond (VHB) acrylic adhesive. In alternative embodiments, one or more other materials and/or thicknesses are used that provide adhesion and/or cushioning such as tapes, epoxies, glues, foams, rubber, neoprene, plastics, hot melts, or the like, depending on the space to be filled, the forces to be measured, the size and weight of components to be stacked together, the amount of freedom of movement needed, the shock and vibration requirements, or the like.

The disk 708 includes a generally cylindrical tang 722 extending from the center of the disk 708 away from the adhesive pad 707. The housing cap 712 includes a generally radially centered hexagonal bore 728 large enough to receive the cylindrical tang 722. The circumference of the housing cap 712 includes a beveled edge 725. The housing cap 712 is placed onto the disk 708 so that the tang 722 is positioned in the hexagonal bore 728, and the beveled edge 722 is facing away from the disk 708.

Figure 8A:
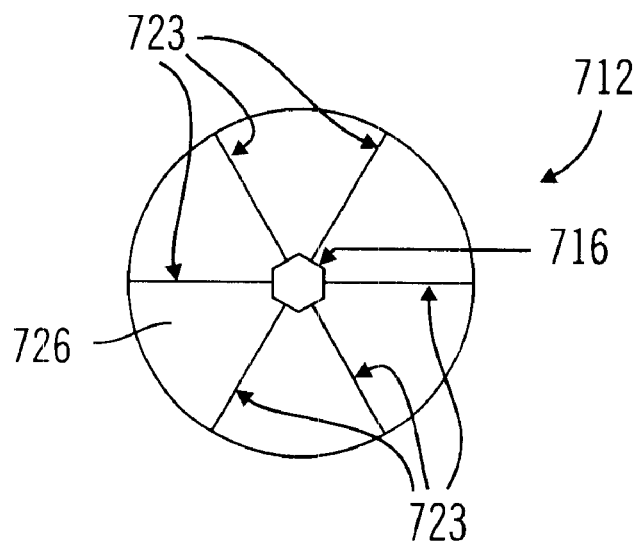
FIG. 8(*a*) is a top view of a disk of the sensing system of FIGS. 7(*a*)–(*d*).
Figure 8B:
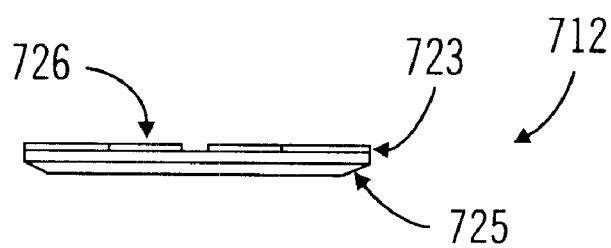
Figure 8C:
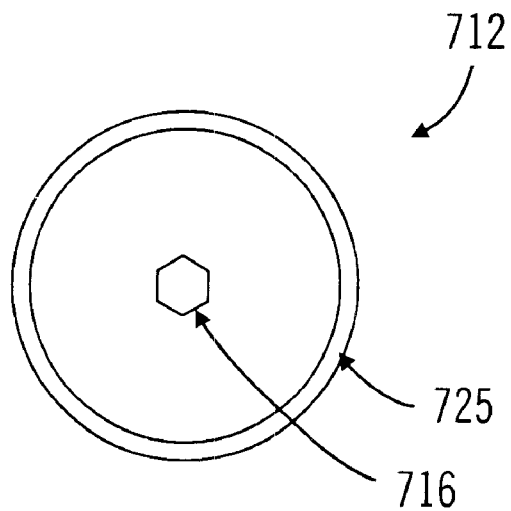

In preferred embodiments, the interior surface 726 (facing the disk 708) of the housing cap 712 includes ridges 723 that extend radially from one or more of the flat edges of the hexagonal bore 728 to the circumference of the housing cap 712, as shown in FIGS. 8(a–b). The ridges 723 hold the housing cap 712 away from the surface of the disk 708 to create space for adhesive. Adhesive is inserted through the hexagonal bore 728, at each of the corners, where there is space between the hexagonal bore 728 and the tang 722. Adhesive inserted at the hexagonal bore 728 spreads radially out to the edges of the disk 708 and the housing cap 712, filling the space between each of the ridges 723. In preferred embodiments, the housing cap 712 is clear so that an assembler can observe the quality of the adhesive coverage between the housing cap 712 and the disk 708, and so that ultraviolet-light-cured adhesive may be used.

In alternative embodiments, the bore in the housing cap has a shape other than hexagonal, such as triangular, square, pentagonal, polygonal, circular, irregular, star shaped, or the like. In other alternative embodiments, the tang on the disk may have other shapes, such as triangular, square, pentagonal, polygonal, circular, irregular, star shaped, or the like. In further alternative embodiments, other methods may be used to hold the housing cap off of the surface of the disk, such as dimples, grooves, flutes, bumps, texturing, broken ridges, or the like. In still further alternative embodiments, other bonding methods may be used such as epoxy, hot melt, tape, contact cement, other adhesives, or the like.

In preferred embodiments, once the housing cap 712 is secured to the disk 708, a force is applied to the housing cap 712 to assure that the shoulder 719 on the motor assembly 705 is seated against the lip 720 in the housing 702, and that space between components stacked between the motor assembly 705 and the housing cap 708 is substantially removed. The force is then removed, so that sensor 706 is not subjected to a preload, and the housing cap 712 is bonded to the housing bottom 703. Preferably, adhesive is applied along the beveled edge 725 of the housing cap 712 to fill the space between the housing cap 712 and the housing bottom 703. Optionally, a label 724 is placed over the housing cap 712.

In alternative embodiments, several components are assembled together before being placed into the housing. For example, the motor assembly 705, sensor 706, adhesive pad 707, and disk 708 may be assembled together and then placed into the housing 702 followed by the housing bottom 703 and then the housing cap 712. In other alternative embodiments, fewer parts are used. For example, a sensor may include a rigid backing obviating the need for a disk. Or a housing bottom may not have an opening for a housing cap, so all of the components are installed into the housing and the housing bottom is positioned to remove spaces between the components and then secured to the housing. In still further alternative embodiments, the force applied to remove space between components is not removed before the housing cap is secured to the housing bottom. In particular alternative embodiments, the preload on the sensor is used to confirm that the space between the components is removed.

Although the foregoing describes one method of assembly, it can be appreciated by those skilled in the art that alternative assembly methods may be employed without departing from the spirit of the invention.

Figure 9:
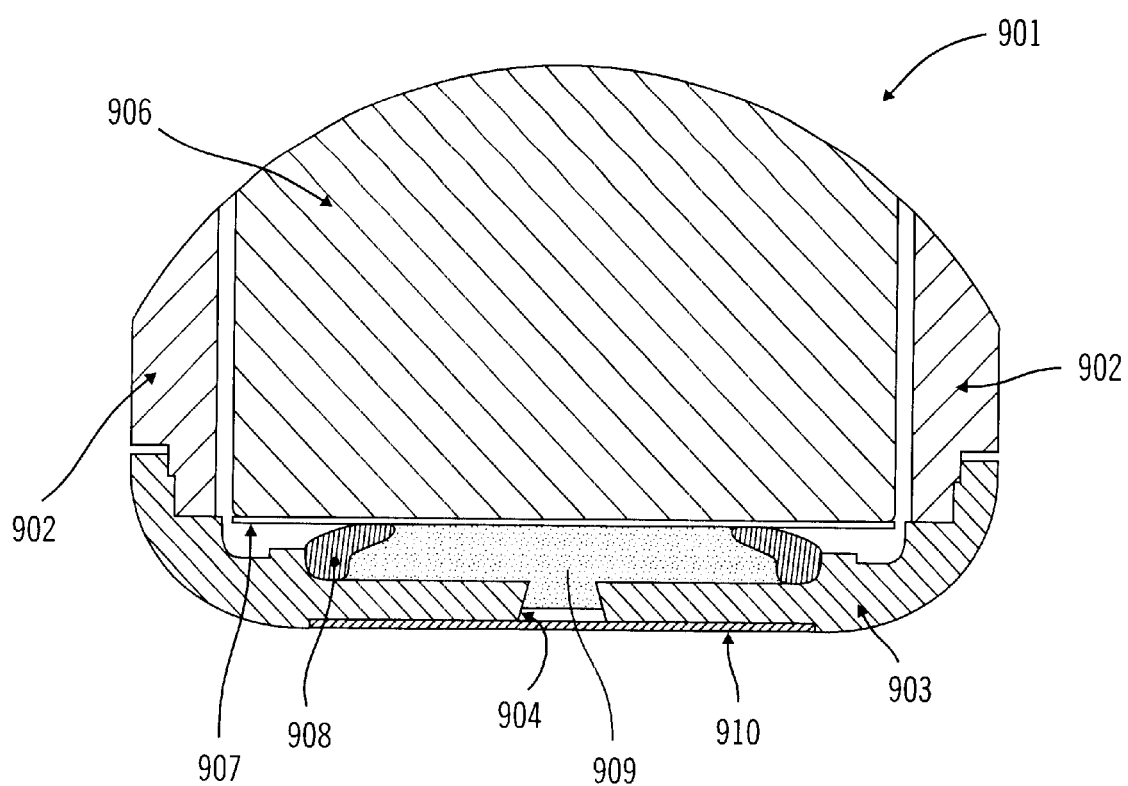
FIG. 9 is an enlarged, cross-sectional view of a sensor system according to a fifth embodiment of the present invention.

In alternative embodiments, a compressible member is used to compensate for tolerance stack-up when assembling a sensor 907 with a motor assembly 906, as shown in FIG. 9. An infusion pump 901 includes a housing bottom 903 attached to a housing 902, which encloses the motor assembly 906. The generally planar-shaped sensor 907 is positioned in direct contact with the motor assembly 906. The compressible member is a flexible silicone rubber seal 908 disposed between the outer edge of the sensor 907 and the housing bottom 903. Before assembly, the seal 908 is generally annular with a generally circular cross-section. When the seal 908 is placed on the sensor 906, and the housing bottom 903 is welded or otherwise attached to the main housing assembly 902, the seal 908 becomes deformed and adapts to the available space to form a water resistant seal between the sensor 907 and the housing bottom 903. The space filled by the seal 908 varies due to the dimensional tolerance stack-up of drive train components (not shown), the sensor 907, the housing 902, and the housing bottom 903. The housing bottom 903 includes an opening 904 generally in line with the axis of rotation of the motor assembly 906. A compliant back-fill material 909, such as silicone, urethane, hot melt adhesive, complaint epoxy, or the like, is injected through the opening 904 to fill the space between the sensor 907 and the housing bottom 903. The back-fill material 909 is substantially incompressible in the axial direction so that forces applied to the sensor 907 by the drive system are not relieved by the back-fill material 909. Furthermore, the back-fill material 909 mechanically isolates the drive system from shock and vibration of the housing 902 and housing bottom 903. In further alternative embodiments, one or more vents (not shown) are provided in the housing bottom 903 to permit venting of air and improve dispersion of the material 909 as the material 909 is injected into the center opening 904 and flows radially outward to the seal 908. The seal 908 serves as a dam to prevent the material 909 from spreading around the motor assembly 906 and into other areas within the housing 902. Once cured, the material 909 helps to absorb shock loads, dampen vibrations, compensate for tolerance stack-up, resist water penetration, and provide an even load distribution across the sensor 907. Optionally, a label 910 is placed on the exterior of the housing bottom 903 over the opening 904.

In preferred embodiments, the sensor and associated electronics provide a relatively linear voltage output in response to forces applied to the sensor by one or more drive train components. Particular preferred embodiments employ the sensor 706 shown in FIGS. 6(*b*), and 7(*a*)–7(*d*). An example of measured voltages from the sensor 706, (and its associated electronics) in response to forces ranging from 0.5 pounds to 4.0 pounds, are shown as data points 201–208 in FIG. 10.

Figure 10:
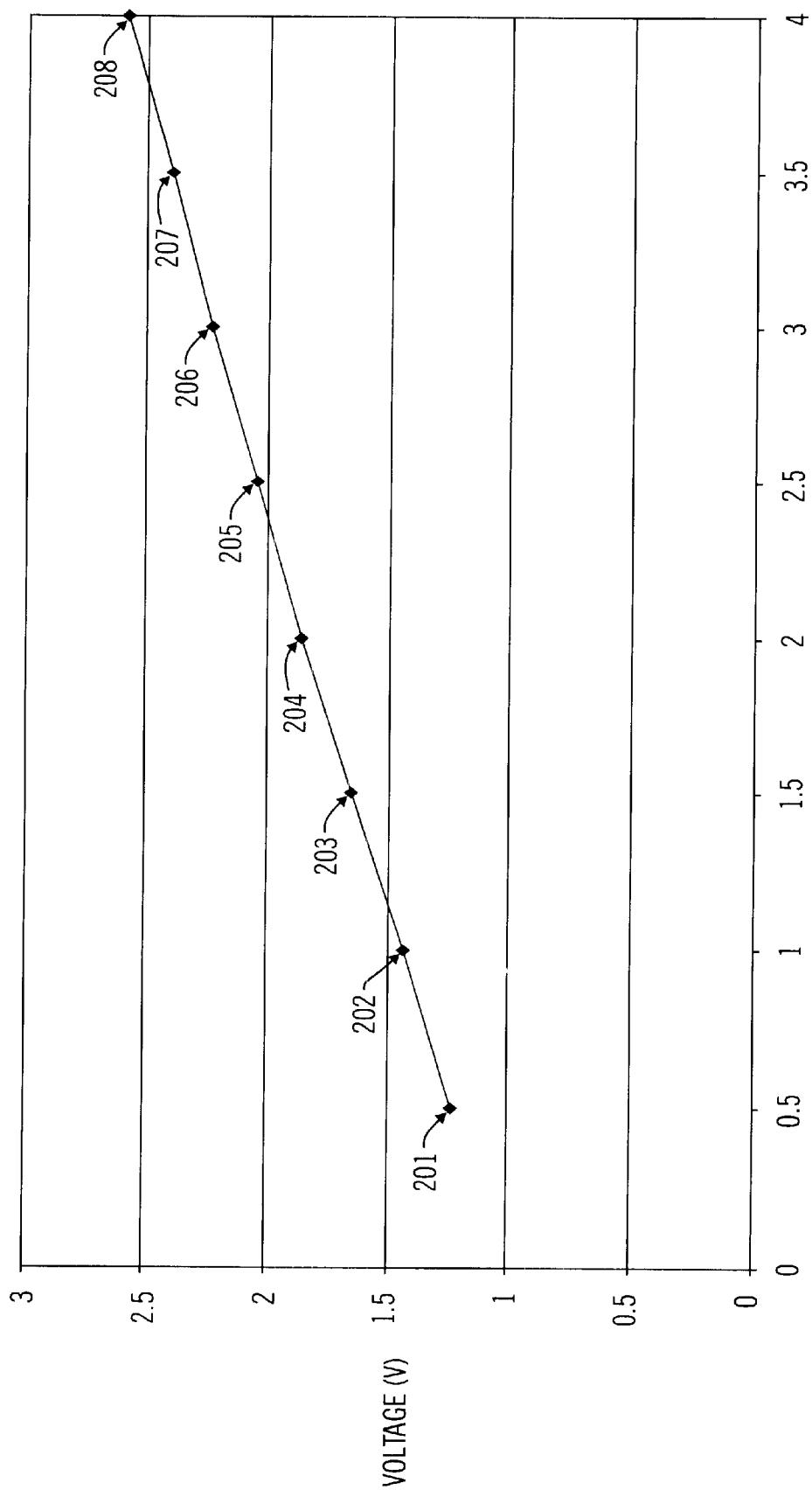
FIG. 10 is a graph showing measured voltage across the force sensitive resistor of FIG. 6(*b*) as a function of applied force.

In preferred embodiments, each sensor is calibrated by collecting calibration points throughout a specified range of known forces, such as shown in FIG. 10. A measured voltage output for each known force is stored in a calibration lookup table. Then, during pump operation, the voltage output is compared to the calibration points, and linear interpolation is used convert the voltage output to a measured force. Preferably, eight calibration points are used to create the calibration lookup table. Alternatively, more or fewer calibration points are used depending on, the sensor linearity, noise, drift rate, resolution, the required sensor accuracy, or the like. In other alternative embodiments, other calibration methods are used such as, curve fitting, a look up table without interpolation, extrapolation, single point calibration, or the like. In further alternative embodiments, the voltage output in response to applied forces is substantially non-linear. In further alternative embodiments, no calibrations are used.

In preferred embodiments, sensor measurements are taken just prior to commanding the drive system to deliver fluid, and soon after the drive system has stopped delivering fluid. In alternative embodiments, sensor data is collected on a continuous basis at a particular sampling rate for example 10 Hz, 3 Hz, once every 10 seconds, once a minute, once every five minutes, or the like. In further alternative embodiments, the sensor data is only collected just prior to commanding the drive system to deliver fluid. In still further alternative embodiments, sensor data is collected during fluid delivery.

In preferred embodiments, two methods are employed to declare occlusions in the fluid path, a maximum measurement threshold method, and a slope threshold method. Either method may independently declare an occlusion. If an occlusion is declared, commands for fluid delivery are stopped and the infusion pump provides a warning to the user. Warnings may include but are not limited to, sounds, one or more synthesized voices, vibrations, displayed symbols or messages, lights, transmitted signals, Braille output, or the like. In response to the warnings, the user may choose to replace one or more component in the fluid path including for example the infusion set, tubing, tubing connector, reservoir, stopper, or the like. Other responses that the user might have to an occlusion warning include: running a self test of the infusion pump, recalibrating the sensor, disregarding the warning, replacing the infusion pump, sending the infusion pump in for repair, or the like. In alternative embodiments, when an occlusion is detected, attempts for fluid delivery are continued, and a warning is provided to the user or other individuals.

When using the maximum measurement threshold method, an occlusion is declared when the measured force exceeds a threshold. In preferred embodiments, a threshold of 2.00 pounds (0.91 kg) is compared to force values measured by the sensor before delivery of fluid. If a measured force is greater than or equal to 2.00 pounds (0.91 kg), one or more confirmation measurements are taken before fluid delivery is allowed. If four consecutive force measurements exceed 2.00 pounds (0.91 kg), an occlusion is declared. In alternative embodiments, a higher or lower threshold may be used and more or less confirmation readings may be collected before declaring an occlusion depending upon the sensor signal to noise level, the electronics signal to noise level, measurement drift, sensitivity to temperature and/or humidity, the force required to deliver fluid, the maximum allowable bolus, the sensor's susceptibility to shock and/or vibration, and the like. In further alternative embodiments, the maximum measurement threshold method is not used.

As mentioned previously, the use of sensors, which provide a spectrum of output levels, rather than a switch, which is capable of providing only two discrete output levels, allows the use of algorithms to detect trends in the output, and thus, declare an occlusion before the maximum measurement threshold is reached. In preferred embodiments, the slope threshold method is used to evaluate trends to provide early occlusion detection. When using the slope threshold method, an occlusion is declared if a series of data points indicate that the force required for fluid delivery is increasing. A slope is calculated for a line passing through a series of consecutive data points. If the slope of the line exceeds a slope threshold, then pressure is increasing in the fluid path, and therefore, an occlusion may have developed. When nothing is blocking the fluid path, the force measured by the sensor before each delivery remains constant.

Figure 11:
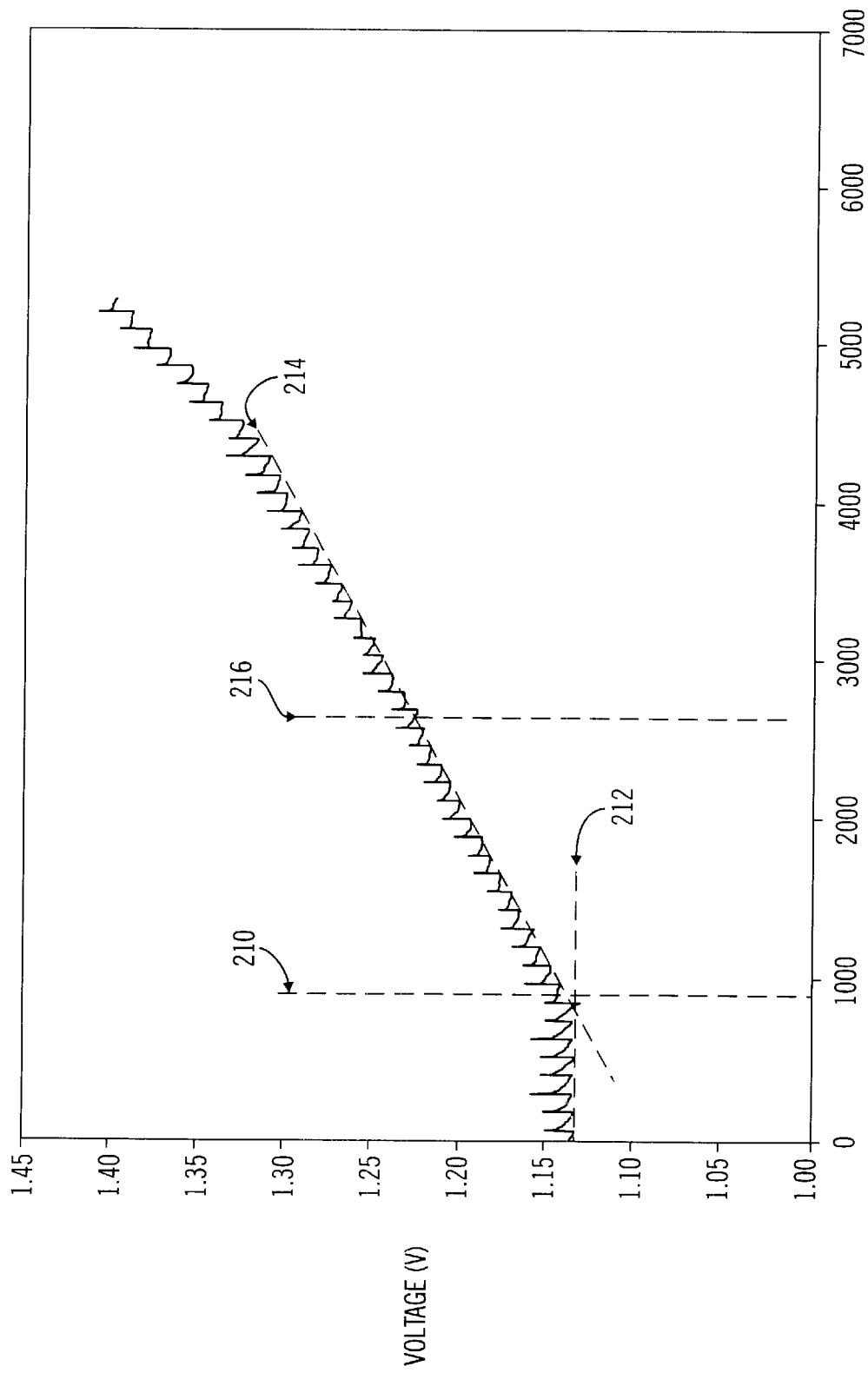
FIG. 11 is a graph showing measured voltage across the force sensitive resistor of FIG. 6(b) during operation of the drive system shown in FIGS. 7(a)–(d).

During fluid delivery, when the drive system moves the stopper forward within the reservoir, the force temporarily and rapidly increases. Then as the fluid moves out of the fluid path, through the cannula and into the body, the force returns to a similar level as measured before fluid delivery was initiated. As an example, a plot of the voltage output, collected at a sample rate of 3 Hz during a series of fluid deliveries, is shown in FIG. 11. The sawtooth appearance of the voltage plot is the result of the sharp increases and slow decay of the force measured by the sensor when the drive system is activated followed by fluid flowing from the infusion pump or relief due to compliance.

The bottom of each sawtooth represents the static force measured before fluid delivery is begun. Initially, the fluid path is free of occlusions. Voltage samples measured before line 210 are values measured before the fluid path is blocked. The static force measurements taken before the fluid path is blocked are similar, and the slope of a line 212 drawn through those static force measurements is approximately or near zero. In other words, there is no occlusion in the fluid path, and the fluid pressure returns to the same offset value after each delivery. However, after line 210 (when the fluid path is blocked) the static force increases after each fluid delivery. The slope of a line 214 drawn through the static force measurements after line 210, is now greater than zero. The voltage output is generally proportional to the force applied to the sensor.

In preferred embodiments, if the measured static force increases by more than 0.05 pounds (0.23 kg) on average for each of 15 consecutive deliveries, an occlusion is declared. Given the example shown in FIG. 11, if we assume that a voltage output of 1.0 volts is equal to or less than 1.0 pound (0.45 kg) of force on the sensor, then it is clear that the slope threshold method is likely to declare the occlusion significantly sooner than the maximum measurement value of 2.00 pounds (0.91 kg) is obtained. The slope threshold method would declare an occlusion at about line 216, while the maximum measured threshold method would not have declared an occlusion even at the highest measurement on the page. Lowering the maximum measurement threshold might help to declare an occlusion sooner, but the drive systems in some infusion pumps are likely to have more friction than others. And the friction of the drive train may change over an extended period of use. So, if the maximum measurement threshold is set too low, occlusions maybe inadvertently declared in pumps that have higher than average friction in the drive system.

In alternative embodiments, larger or smaller changes in force over a larger or smaller number of measurements is used to declare an occlusion depending upon the force measurement resolution, the signal to noise ratio in the voltage output, friction in the drive train, the maximum allowable delivery, or the like. In further alternative embodiments, the slope is calculated from force or voltage values that are collected at times other than prior to fluid delivery such as, after fluid delivery, during fluid delivery, randomly, continuously, or the like. In still further alternative embodiments, other algorithms may be employed to calculate a slope or evaluate the difference between one measurement and another, such as using differential values rather than actual measured values, calculating the derivative of measured values, using a subset of points across the range of points to calculate the slope, using curve fitting equations, employing smoothing, clipping or other filtering techniques, or the like.

In particular alternative embodiments, the static force must exceed a minimum threshold and the slope must exceed a maximum value for an occlusion to be declared. For example, an occlusion is only declared if the last force measurement is greater than 1.00 pound (0.45 kg) and the slope is greater than 0.05 on average for each of the last 15 measurements (generally associated with the last 15 deliveries).

In particular embodiments, an occlusion is declared if an average slope (A) exceeds a slope threshold of 0.05. The Current Slope (S) is calculated as:

$$S=F(0)-F(-5).$$

Where F(0) is a current force measurement, and F(−5) is a force measurement taken 5 measurements previously.
And the Average Slope (A) is:

$$A=A(-1)+W*(S-A(-1)).$$

Where A(−1) is the average slope calculated at the previous force measurement, W is a weighting factor of 0.30, and S is the current slope.

In other particular embodiments, and occlusion is declared if the average slope (A) is greater than a slope threshold of 0.05 for 15 measurements in a row. And if the average slope (A) drops below 0.05 for 4 measurements in a row, then restart counting. Measurements are taken just prior to each delivery. A delivery is defined as an incremental motor activation to dispense a controlled dose of fluid. In particular embodiments, after each measurement, a counter is incremented if the average slope exceeds the slope threshold. If the counter reaches a detection count value, then an occlusion is declared.

In alternative embodiments, the measured values used to calculate the current slope are separated by a greater or smaller number of measurements. In further alternative embodiments, the weighting factor W is larger or smaller depending on the previous average slope A(−1), the current force reading F(0), the accuracy of the measurements, and the like. And in other alternative embodiments, the slope threshold is greater or smaller depending on the concentration of the fluid, the maximum allowable bolus, the sensor accuracy, the signal to noise ratio, and the like. In still further alternative embodiments, one or more of the measured force values must meet or exceed 1.00 pound before the slope threshold method can declare an occlusion. For example, in some embodiments, the last four force measurements must be greater than 1.00 pound and the average slope must exceed 0.05 over the last 15 force measurements to declare an occlusion. In other alternative embodiments, the detection count value may be higher or lower depending on the sensor accuracy, the level of shock and vibration effects, the required range of measurement, and the like.

In further particular embodiments, the number of deliveries per measurement is dependent on the concentration of the fluid being delivered. For example, when delivering a U200 insulin formula, a measurement is taken with each delivery, when delivering a U100 insulin formula, a measurement is taken every two deliveries, and when delivering a U50 insulin formula, a measurement is taken every 4 deliveries.

In alternative embodiments, other algorithms are used to calculate a slope from the sensor measurements to compare to a slope threshold. Other algorithms include, but are not limited to, a least squares line fit through a number of measurements, averaging two or more groups of measurements and then calculating the slope of a line through the averaged values, regression algorithms, or the like.

In still other alternative embodiments, the current force measurement is compared to one or more previous force measurements, or to a trend observed from force measurements, to determine whether the current force measurement is valid (representative of a force applied to the drive train by the motor). If the current force measurement is not valid, it is ignored, replaced, re-measured, or the like.

While the specific embodiments illustrated herein generally pertain to medication infusion pumps, the scope of the inventions in one aspect is much broader and may include any type of fluid pump medical system.

In particular embodiments, the sensor is used to detect the removal of one or more components in the fluid path such as disconnecting the infusion set, disconnecting the tubing, or the like. During normal operation, the sensor is subjected to a nominal force due to the sum of the system frictional components, the hydrodynamic forces associated with delivering a fluid through tubing, and the backpressure associated with the infusion set inserted in the patient. The nominal force is represented by a voltage offset such as represented by line 212 in FIG. 11. If a component in the fluid path were removed, the fluid backpressure would decrease thereby reducing the nominal force on the sensor. The infusion pump provides a warning to the user when the nominal force on the sensor decreases below a threshold, decreases by a particular percentage, decreases over a series of measurements, or the like. In alternative embodiments, larger or smaller decreases in the nominal force on the sensor are used to detect leaks in the fluid path.

In other particular embodiments, a sensor is used to detect when a reservoir is empty. An encoder is used to measure motor rotation. The encoder counts increase as the motor operates to move a stopper deeper into the reservoir. The encoder counts are used to estimate when the stopper is nearing the end of the reservoir. Once the encoder counts are high enough, if an occlusion is detected due to increased force on the sensor, the reservoir is declared empty.

Figure 7A:
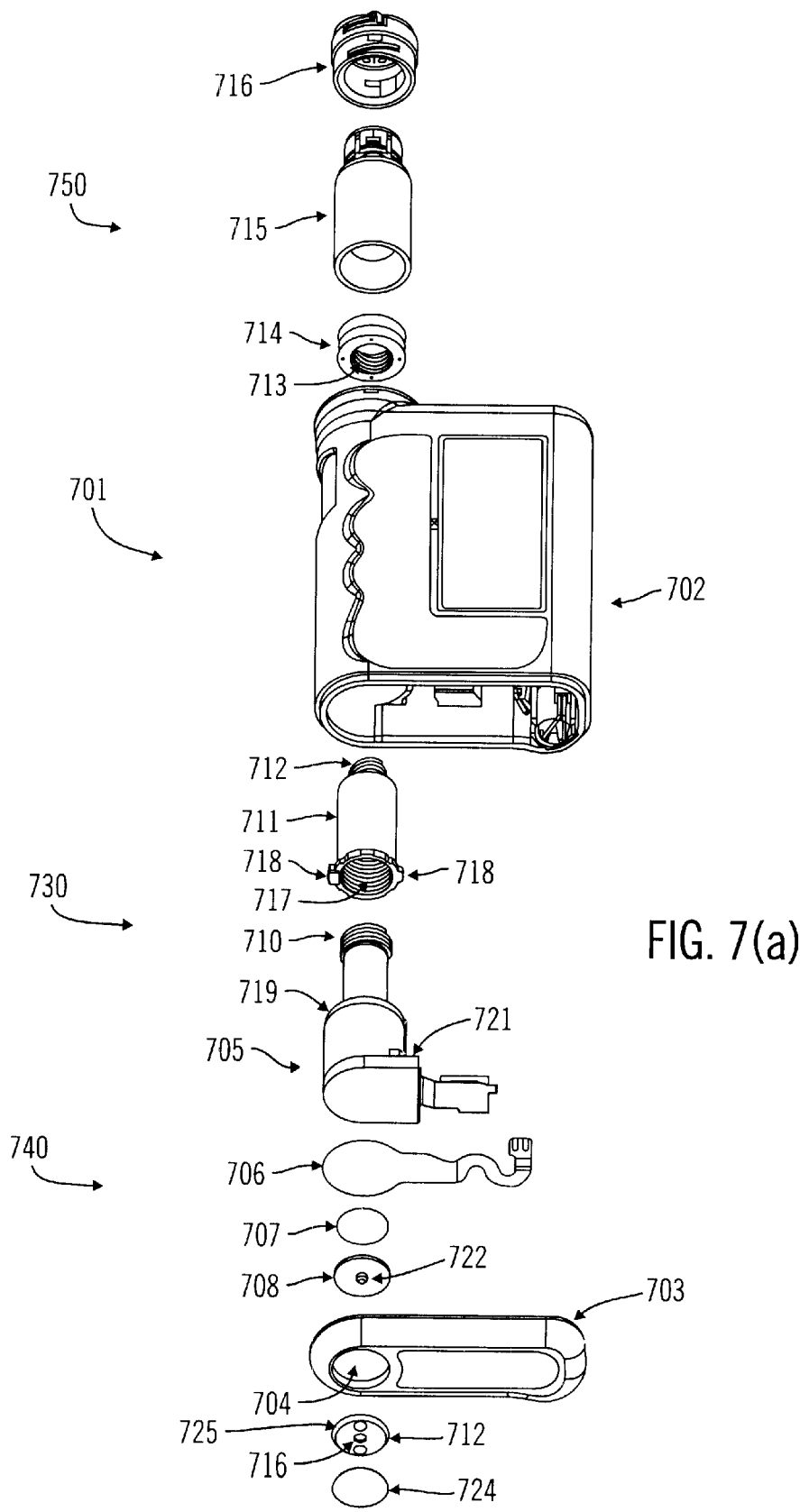
FIG. 7(*a*) is an exploded bottom/front perspective view of an infusion pump drive system, sensing system, and fluid containing assembly, incorporating the sensor of FIG. 6(*b*).
Figure 7B:
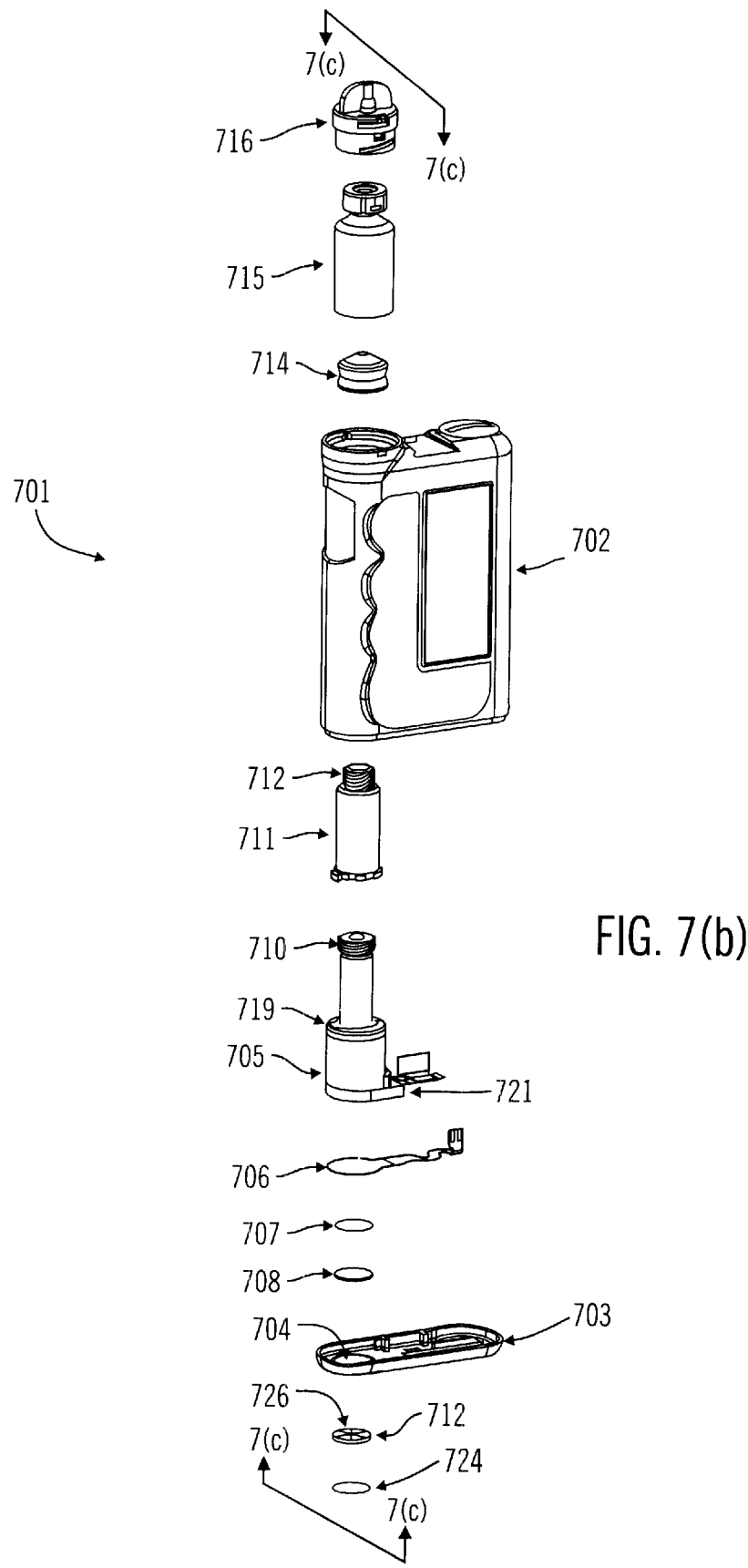
Figure 7C:
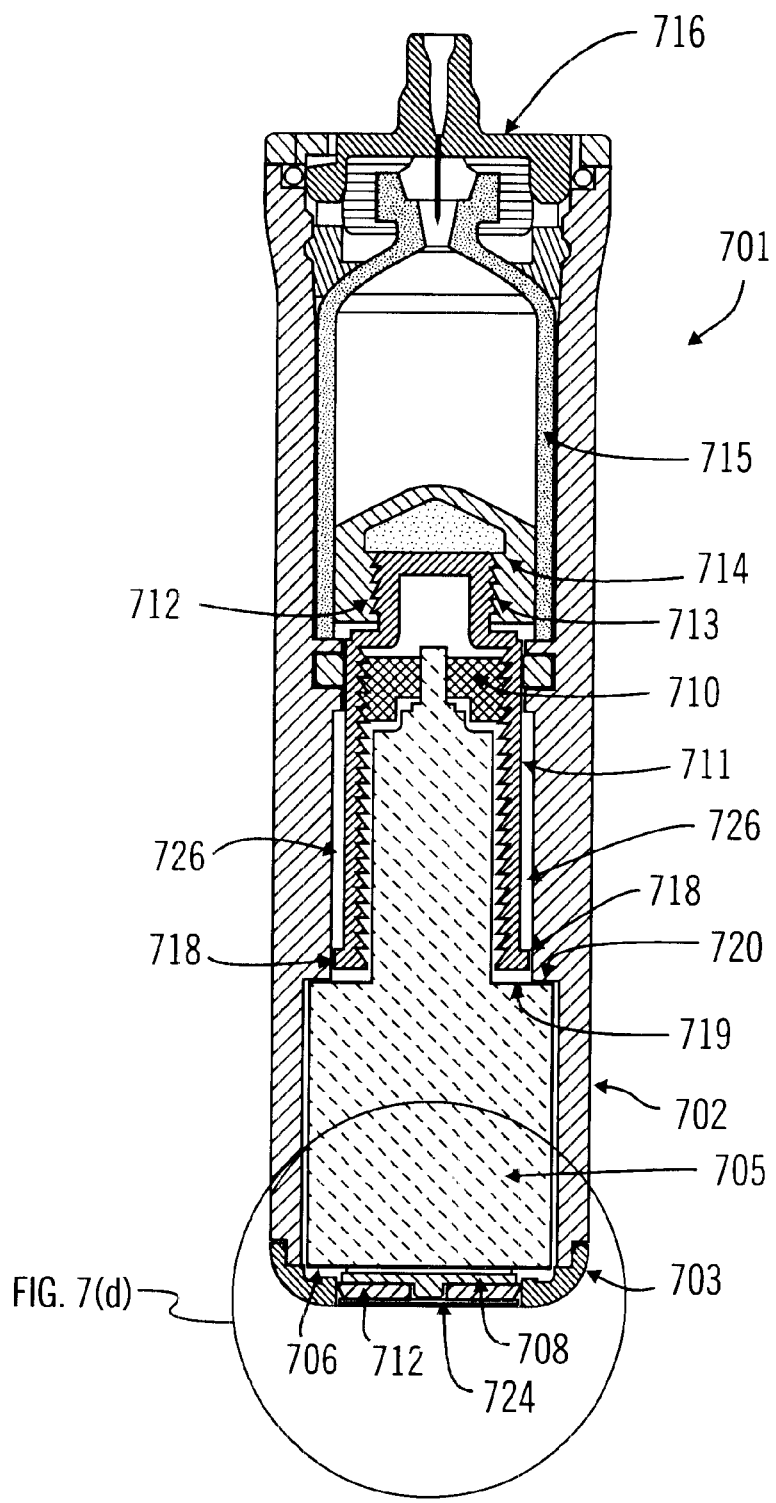
Figure 7D:
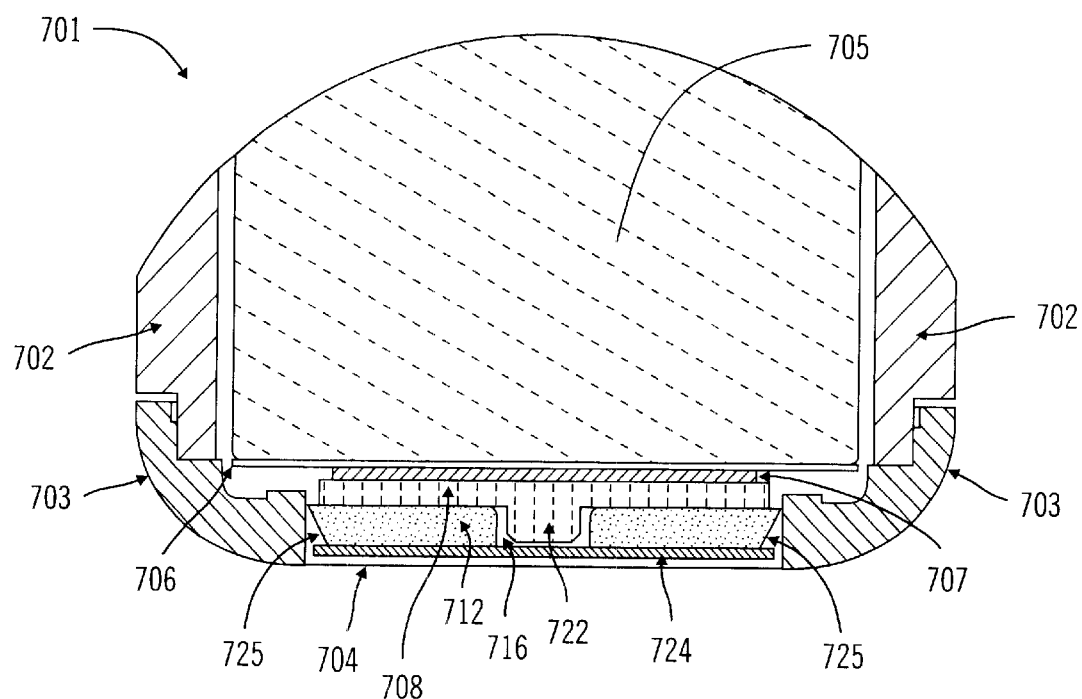

In other particular embodiments, a sensor 706 is used to detect when a slide 711 is properly seated with a stopper 714, as shown in FIG. 7(a). The reservoir 715 containing the stopper 714 is filled with fluid before it is placed into an infusion pump 701. The stopper 714 has pliable internal threads 713 designed to grip external threads 712 on the slide 711. The stopper 714 and slide 711 do not need to rotate with respect to each other to engage the internal threads 713 with the external threads 712. In fact, in particular embodiments, the internal threads 713, and the external threads 712, have different thread pitches so that some threads cross over others when the slide 711 and stopper 714 are forced together. Once the reservoir 715 is placed into the infusion pump 701, a motor 705 is activated to move the slide 711 into the reservoir 715 to engage the stopper 714. As the threads 712 of the slide 711 first contact the threads 713 of the stopper, a sensor 706 detects an increase in force. The force continues to increase as more threads contact each other. When the slide 711 is properly seated with the stopper 714, the force measured by the sensor 706 increases to a level higher than the force needed to engage the internal threads 713 with the external threads 712. During the seating operation, if the force sensed by the sensor 706 exceeds s seating threshold, the motor 705 is stopped until further commands are issued. The seating threshold is generally about 1.5 pounds (0.68 kg). In alternative embodiments higher or lower seating thresholds may be used depending on the force required to mate the slide with the stopper, the force required to force fluid from the reservoir, the speed of the motor, the sensor accuracy and resolution, or the like.

In still other particular embodiments, other force thresholds are used for other purposes. During priming for example, a threshold of about 4 pounds (2 kg) is used. In alternative embodiments, forces greater than about 4 pounds are used to detect shock loads that may be damaging to an infusion pump.

Typically, over a long enough period of operation, sensors suffer from drift. In preferred embodiments, drift measurements are taken though the life of a statistically significant number of sensors to generate a drift curve. The drift curve is used to compensate for drift in sensors used in infusion pumps. For example, a lookup table of force offset (due to drift) over operation time is stored in the infusion pump. The offset values are used to compensate the force measurements over time. In alternative embodiments, the drift is characterized by an equation rather than a lookup table. In other alternative embodiments, the sensor is periodically re-calibrated. In still other alternative embodiments, the sensor does not drift or the drift is insignificant enough that no compensation is needed.

In further alternative embodiments, drift is compensated relative to the number of deliveries, the number of reservoir replacements, the integral of the forces placed on the sensor, or the like.

Particular sensors used to detect occlusions suffer from temperature and/or humidity shifts. In preferred embodiments, the infusion pump includes humidity and/or temperature sensors. Measurements from the humidity and/or temperature sensors are used to compensate the sensor output. In alternative embodiments, humidity and/or temperature compensation is not needed.

The use of sensors for detecting characteristics of the drive system and the fluid containing assembly are not limited to the infusion pumps and drive systems shown in the figures. Moreover, the type of sensor need not be confined to a force sensitive resistor as described in preferred embodiments.

Figure 12:
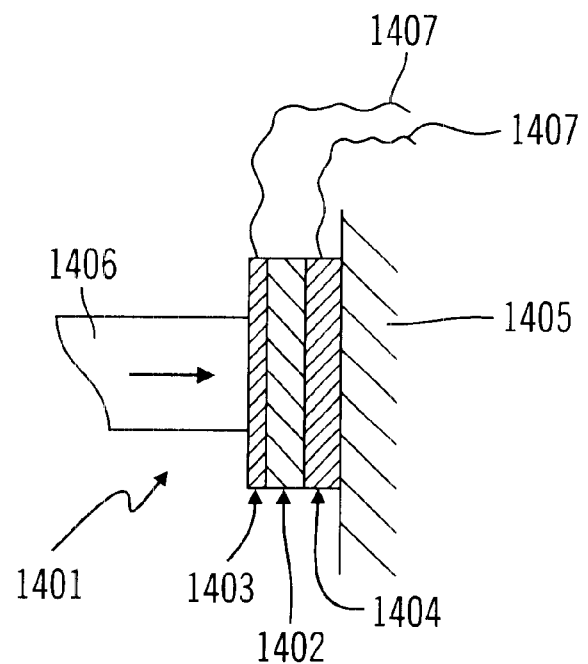
FIG. 12 is a cross sectional view of a capacitive sensor mounted between a drive system component and a housing according a sixth embodiment of the present invention.

In alternative embodiments, a capacitive sensor 1401 is used, such as shown in FIG. 12. A dielectric material 1402 is disposed between a conductive proximate plate 1403 and a conductive distal plate 1404. The distal plate 1404 is secured to a pump housing 1405 or alternatively, to any other stationary component of a medication infusion pump. The proximate plate 1403 is in contact with a drive system lead screw 1406. Alternatively, the proximate plate 1403 could be in contact with a pump motor or any other dynamic drive train component that is subjected to a reactive force correlated to reservoir fluid pressure variations.

As the force applied to the drive train increases, the lead screw 1406 applies greater force to the proximate plate 1403 moving it closer to the distal plate 1404, and partially compressing the dielectric material 1402. As the gap across the dielectric material 1402 decreases, the sensor capacitance increases. The capacitance is expressed by the relationship:

$$C = \frac{k\varepsilon_0 A}{d}$$

where C is the capacitance, $\varepsilon_o$ is the permittivity constant (of free space), A is the surface area of the conductive plates, and d is the distance between the conductive plates. Electrical leads 1407 connect the proximate plate 1403 and the distal plate 1404 to the electronics system (not shown), which measures the varying capacitance. The electronics system and sensor are calibrated by applying known forces to the drive train. Once calibration is complete, the electronics system converts sensor capacitance to force measurements.

Figure 13:
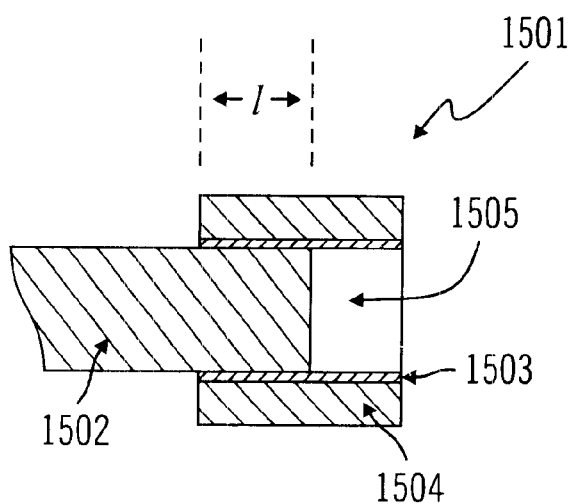
FIG. 13 is a cross-sectional view of a capacitive sensor according a seventh embodiment of the present invention.

In another alternative embodiment, a cylindrical capacitive sensor 1501 includes a conductive rod 1502, a dielectric inner ring 1503 and a conductive outer ring 1504, as shown in FIG. 13. The conductive rod 1502 is connected to a drive system lead screw (not shown). Alternatively, the conductive rod 1502 could be connected to any other dynamic drive train component that experiences movement correlated to a reservoir fluid pressure. Conductive leads (not shown) electrically connect the rod 1502 and the outer ring 1504 to the system electronics.

In particular embodiments, as the fluid pressure increases, the lead screw is axially displaced, which in turn moves the rod 1502 further into the opening 1505 formed by the rings 1503 and 1504. Thus, the surface area of the capacitor increases, thereby increasing capacitance according to the relationship:

$$C = \frac{2\pi k \varepsilon_0 l}{\ln\left(\frac{b}{a}\right)}$$

where C is the sensor capacitance, l is the length of the rod 1502 that is enclosed by the rings 1504 and 1503, a is the radius of the rod 1502, b is the internal radius of the outer ring 1504 and $\varepsilon_0$ is the permittivity of free space. Once calibrated, the electronics system converts the measured sensor capacitance to a force measurement.

Although the use of force sensitive resistors and capacitive sensors have been described above, it should be appreciated that the embodiments disclosed herein include any type of sensor that can provide least three different levels of output signal across the range of intended use. Sensors may be positioned within various embodiments of drive trains to measure either a force applied to a drive train component, a change in position of a drive train component, a torque applied to a drive train component, or the like.

For example, in alternative embodiments a piezoelectric sensor is used to produce varying voltages as a function of varying forces applied to a drive train component. In particular alternative embodiments, the piezoelectric sensor is made from polarized ceramic or Polyvinylidene Floride (PVDF) materials such as Kynar®, which are available from Amp Incorporated, Valley Forge, Pa.

In other alternative embodiments, multi-switch sensors are used. A distinction is made between switches, which have only two distinct output levels, versus sensors, which have more than two output levels. But, multi-switch sensors are sensors made from two or more discrete switches having different actuation set points. Thus, these multi-switch sensors have at least three output levels. In particular alternative embodiments, a sensor 1601 is comprised of five series mounted switches 1602a–1602e, each of which has a different set-point, as shown in FIG. 14(a). A first switch 1602a is positioned in contact with a lead screw 1603, or alternatively, any other drive train component that is subjected to a force correlated with a reservoir fluid pressure. At the opposite end of the series of switches 1602a–1602e, a last switch 1602e is secured to a pump housing 1604 or alternatively, to any other stationary component of an infusion pump. Conductive leads 1605 are attached to each of the switches 1602a–1602e. As the force applied to the lead screw 1603 increases, the switches 1602a–1602e are triggered one after another as their set points are reached. The electronics system (not shown) monitors each switch. In further particular embodiments, the sensor resolution is dependent on the number of switches and the relative force required for triggering each switch, the range of measurements needed, and the like.

In still other alternative embodiments, the sensor incorporates a multi-switch design where a series of switches 1607a–1607e are electrically connected in series, as shown in FIG. 14(b). An electrical lead 1608 connects a first switch 1607a to the electronics system (not shown). Leads 1609 connect each switch 1607a to 1607e in series. Finally, lead 1610 connects a last switch 1607e to the electronics system. All of the switches 1607a–1607e are electrically connected such that continuity exists through each switch regardless of whether a switch is in a first position or a second position (on or off). Otherwise, the series electrical connection would be broken when a switch is opened.

In particular alternative embodiments, each of the switches 1607a–1607e have a first position and a second position, as shown in FIG. 14(c). When in the first position, each switch connects the circuit through a first resistor 1611a–1611e, each of which has a value of R1 ohms. When each switch is subjected to a force at its respective set point, it moves to its second position thereby disconnecting from the first resistor 1611a–1611e, and closing the circuit through a second resistor 1612a–1612e, each having a value of R2 ohms. And R1 does not equal R2. Thus, depending upon the position of each of the switches 1607a–1607e, a different over-all circuit resistance is measured by the electronics system corresponding to the force applied to a drive train component. In further particular alternative embodiments, while the resistance of all of the first resistors R1 is greater than or less than the resistance of all of the second resistors R2, the resistance of each of the first resistors R1 are not equal to each other, and/or the resistance of each of the second resistors R2 are not equal to each other. In other particular embodiments, a switch with the highest set point may not include resistors, but may simply be an on/off switch. In still other embodiments, other electrical components and/or arrangements are used, such as a parallel circuit shown in FIG. 15(c).

Figure 15A:
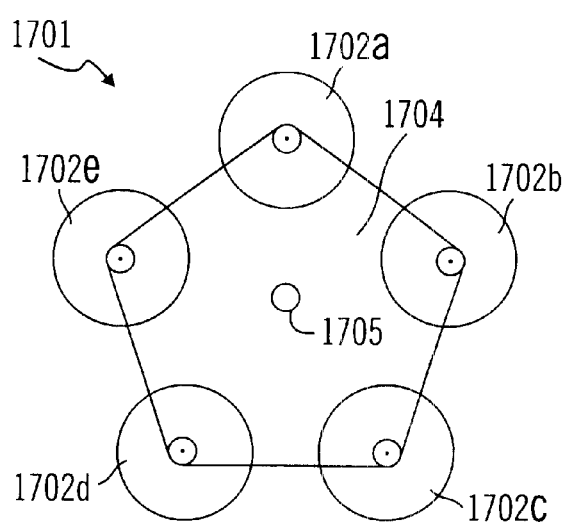
FIG. 15(a) is a top plan view of a multi-switch sensor, where the switches are mounted in parallel.
Figure 15B:
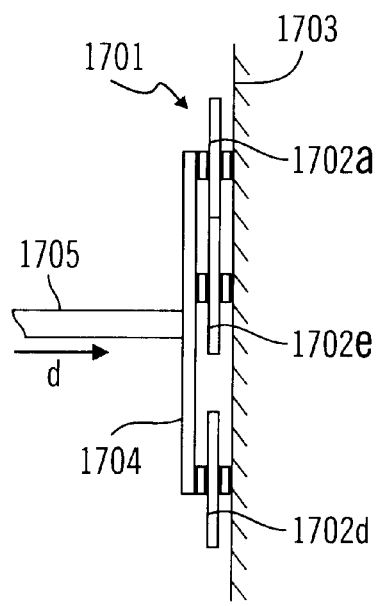
FIG. 15(b) is a side plan view of the multi-switch sensor of FIG. 15(a).

In alternative embodiments, an infusion pump uses a sensor made of two or more multi-switches that are arranged in a parallel circuit. In particular alternative embodiments, a sensor 1701 has five switches 1702a–1702e arranged in parallel, each with a different set point, as shown in FIGS. 15(a) and 15(b). The switches 1702a–1702e are mechanically arranged in parallel such that one side of all five switches 1702a–1702e is in contact with a pump housing 1703, or another member that is stationary with respect to the housing. The opposite side of each of the switches 1702a–1702e is secured to a plate 1704. A drive train component, such as a lead screw 1705, directly or indirectly applies force to the plate 1704. The force is correlated to the fluid pressure in the reservoir (not shown). As the lead screw 1705 moves in direction d, each one of the switches 1702a–1702e will close at different set points depending upon the amount of force exerted on the plate 1704 by the lead screw 1705.

Figure 15C:
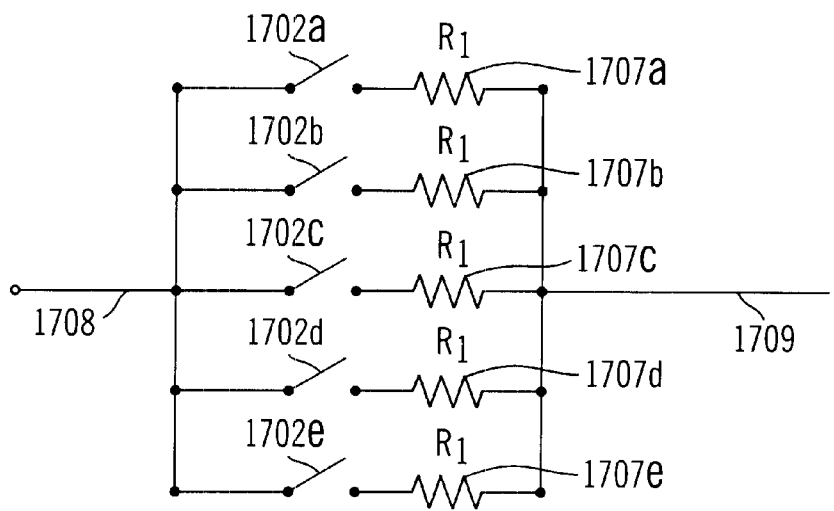
FIG. 15(c) is an electrical schematic for a multi-switch sensor, where the switches are electrically connected in parallel.

The switches 1702a–1702e can be electrically connected to each other and to the system electronics in any number of ways. For example, each switch could be independently connected to the system electronics. Alternatively, the switches 1702a-1702e could be electrically connected in series. In other embodiments each switch 1702a-1702e is associated with a resistor 1707a–1707e, and the switches are connected in parallel, as shown in FIG. 15(c). A conductive lead 1708 provides an input signal from an electronics system (not shown) to the parallel array of switches 1702a–1702e. When the force across a switch reaches the switch set point, the switch closes, and current flows through the resistor 1707a–1707e associated with the switch 1702a–1702e through a lead 1709, and back to the electronics system. As different combinations of switches close, different resistors are placed in parallel in the network, thus changing the impedance of the network. The impedance is measured by the electronics system and converted to measured force that is correlated to fluid pressure.

While the previously described embodiments have illustrated the coupling of various types of sensors to components at the end of a drive train, the scope of the present invention is by no means limited to such locations. Other embodiments include the placement of sensors at or near the front end of a drive train.

Figure 16:
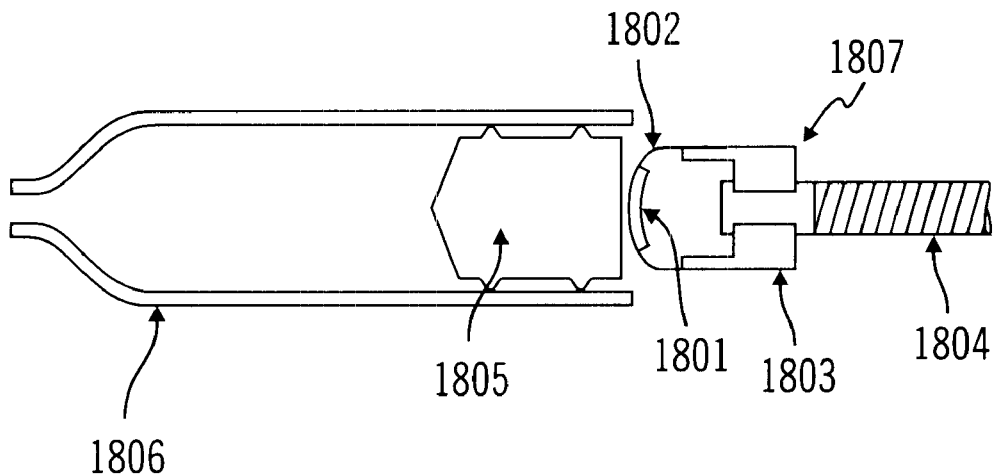
FIG. 16 is an illustration view of a sensor in a pump drive system according to an eleventh embodiment of the present invention.

In particular embodiments, a slide assembly 1807 is comprised of a thin, dome-shaped cap 1802, mounted on a support assembly 1803, and secured to a lead screw 1804, as shown in FIG. 16. A strain gauge sensor 1801 is mounted on the cap 1802. The cap 1802 is constructed of a resilient material, such as silicone, and is in contact with a stopper 1805, which is slidably positioned in a reservoir 1806. As the lead screw 1804 advances, the support assembly 1803 and cap 1802 move axially to contact the stopper 1805, and cause the stopper 1805 to move axially forcing fluid from the reservoir 1806.

The cap 1802 deflects as it is pressed against the stopper 1805. And as the cap 1802 deflects, the dimensions of the strain gauge sensor 1801 are changed, thereby changing the strain gauge impedance. As fluid pressure in the reservoir 1806 increases, the cap 1802 deflection increases, which changes the impedance of the strain gauge sensor 1801. Thus, the strain gauge sensor output impedance is related to the force imposed on the stopper 1805, which is correlated with the reservoir fluid pressure. The electronics system is calibrated to convert the measured strain gauge sensor output impedance to force on the drive train or fluid pressure.

Having the sensor in direct contact with the stopper 1805 ameliorates the effects of dimensional tolerance stack-up and frictional forces within the drive train. This can allow for a more accurate measurement of the pressures within the reservoir 1806. Additionally, since the strain gauge sensor 1801 can provide a range of output levels, software/firmware can be used to set a threshold value that is appropriate for the particular device or drug being infused. Furthermore, over time, the system can calibrate or zero the strain gauge sensor 1801 when there is no reservoir 1806 in place in order to avoid undesirable effects from drift, creep, temperature, humidity, or the like.

Other embodiments of the present invention involving a sensor mounted at or near the front of the drive train are shown in FIGS. 17 to 20.

Figure 17:
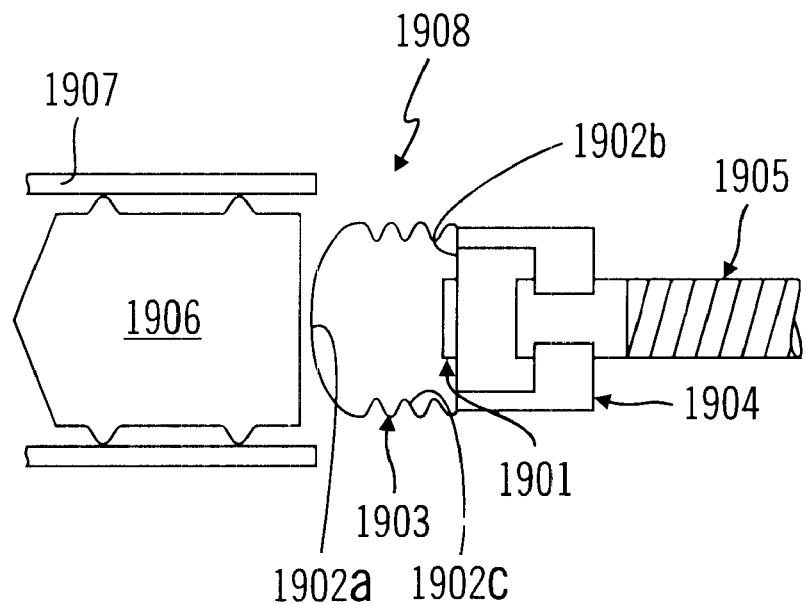
FIG. 17 is an illustration view of a sensor in a pump drive system according to a twelfth embodiment of the present invention.

In a particular embodiment, a slide 1908 includes a strain gauge sensor 1901, a bellows 1903, and a support assembly 1904, as shown in FIG. 17. The bellows 1903 has a proximate wall 1902a, a distal wall 1902b, and a flexible sidewall 1902c. The strain gauge sensor 1901 is mounted on the distal wall 1902b. At least a portion of the perimeter of the distal wall 1902b supported by the support assembly 1904. And the support assembly 1904 is secured to a lead screw 1905. The distal wall 1902b is constructed of a deflectable resilient material, such as silicone, so that as pressure is placed against the proximate wall 1902a, the distal wall 1902b deflects toward the lead screw 1905. The bellows 1903 is driven forward by the lead screw 1905 and support assembly 1904 to push on a stopper 1906 that is slidably positioned in a reservoir 1907. As the lead screw 1905 continues to advance, the bellows 1903 pushes on the stopper 1906 to force fluid from the reservoir 1907. The bellows 1903 may be filled with a fluid to improve the transfer of pressure from the proximate wall 1902a to the distal wall 1902b. The amount of distal wall 1902b deflection is correlated with the force required to move the stopper 1906. The strain gauge sensor output is correlated with the amount of distal wall 1902b deflection. The electronics system converts the strain gauge sensor output to an estimate of force or pressure exerted by the drive system to deliver fluid.

Figure 18:
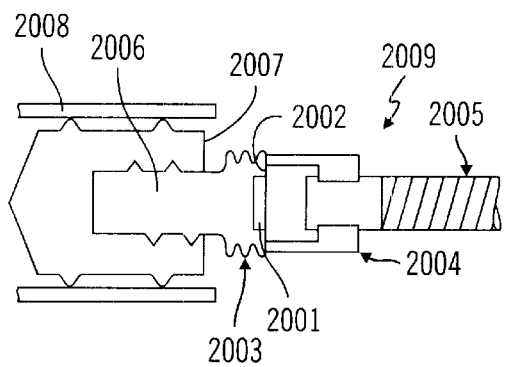
FIG. 18 is an illustration view of a sensor in a pump drive system according to a thirteenth embodiment of the present invention.

In similar particular embodiments, a slide 2009 is comprised of a strain gauge sensor 2001, a support assembly 2004 and a resilient bellows 2003 having a threaded member 2006, as shown in FIG. 18. The strain gauge sensor 2001 is mounted on a distal wall 2002 of the bellows 2003. The support assembly 2004 supports at least a portion of the perimeter of the distal wall 2002 of the bellows 2003, and couples a lead screw 2005 with the bellows 2003. The threaded member 2006 of the bellows 2003 is removably secured to a stopper 2007 that is slidably positioned in a reservoir 2008. This allows for bi-directional displacement of the stopper 2007 by the drive system as well as helping to prevent the unintended advancement of the stopper 2007 due to forces on the reservoir 2008 other than lead screw 2005 advancement, such as differential air pressure, or the like. As the stopper 2007 is pushed or pulled by the drive system, the distal wall 2002 is deflected one way or another. The output of the strain gauge sensor 2001 varies with the deflection of the distal wall 2002, and the electronic system converts the strain gauge sensor output to estimates of force or pressure applied to the stopper 2007 by the drive system.

Figure 19:
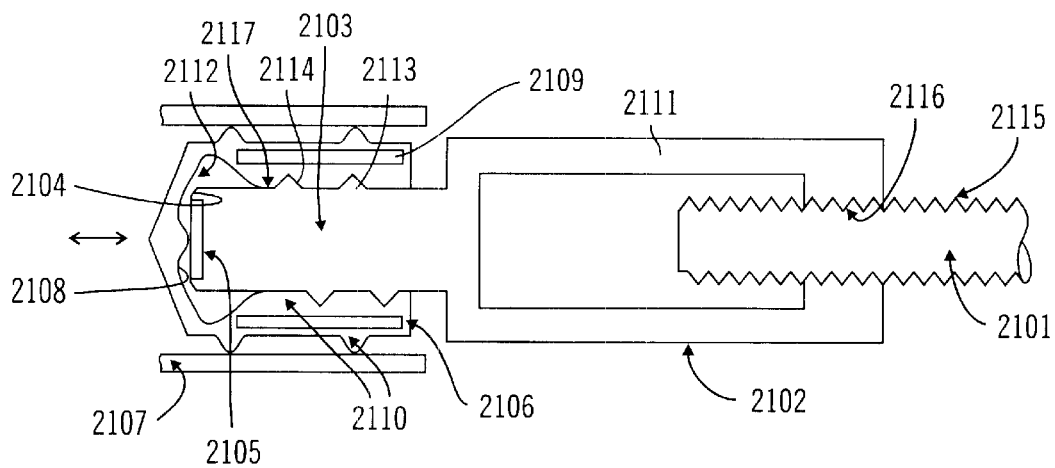
FIG. 19 is an illustration view of a sensor in a pump drive system according to fourteenth embodiment of the present invention.
Figure 20:
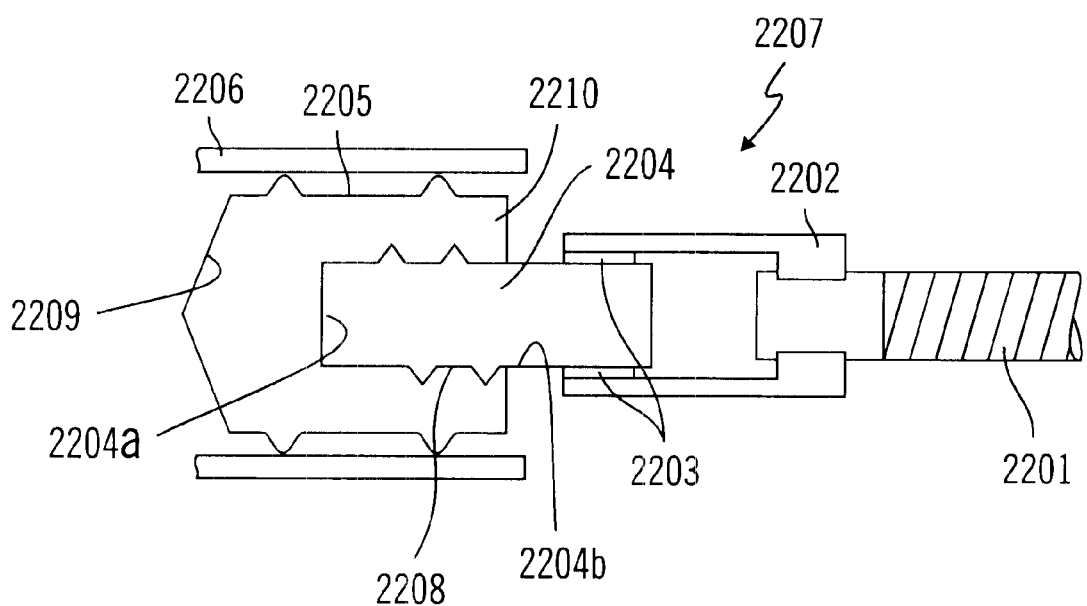
FIG. 20 is an illustration view of a sensor in a pump drive system according to a twentieth embodiment of the present invention.

In an alternative embodiment, external threads 2115 of a lead screw 2101 are engaged with the internal threads 2116 of a slide 2102 to convert the rotational motion of the lead screw 2101 to translational motion of the slide 2102, as shown in FIG. 19. The slide 2102 has a nose 2103 formed by a relatively stiff generally cylindrical sidewall 2117 and a proximate nose wall 2104 made of a flexible material such as silicone. A strain gauge sensor 2105 is secured to the proximate nose wall 2104. The slide 2102 is removably coupled to a stopper 2106 slidably positioned in a fluid reservoir 2107. The stopper 2106 has a cavity 2112 formed by an internally threaded cylindrically-shaped sidewall 2110, which forms a water-tight seal with the reservoir 2107, and a flexible proximate wall 2108. The cavity 2112 is adapted to receive the nose 2103, so that the proximate wall 2108 of the cavity 2112 abuts the proximate nose wall 2104 of the nose 2103. The nose sidewall 2117 has external threads 2113 for removably engaging the internal threads 2114 on the sidewall 2110 of the stopper cavity 2112. The threaded coupling between the slide 2102 and the stopper 2106 enables the drive system to move the stopper 2106 bi-directionally. A reinforcing ring 2109 is disposed in the stopper sidewall 2110 to provide the necessary stiffness to maintain a frictional fit between the stopper 2106 the reservoir 2107, thereby enhancing a watertight seal. In further alternative embodiments, the reinforcing ring 2109 is not needed.

As the flexible proximate wall 2108 of the stopper 2106 deflects due to fluid pressure, it contacts the proximate nose wall 2104 causing it to deflect, thus deflecting the strain gauge sensor 2105. This provides a measurement of the pressure within the reservoir 2107 independent of the force used to drive the stopper 2106. This sensor placement provides a true indicator of pressure within the reservoir 2107. The frictional forces between the stopper 2106 and the reservoir 2107, as well as between other drive train components are not measured, and therefore do not affect the measurement of the fluid pressure.

In particular alternative embodiments, measurements from the strain gauge sensor 2105 are used to confirm correct reservoir 2107 installation. If the reservoir 2107 is installed into the infusion pump properly and the slide 2102 is fully engaged with the stopper 2106 within the reservoir 2107, then the stopper 2106 applies at least a slight contact with the proximate nose wall 2104 imparting a preload on the strain gauge sensor 2105. If the reservoir 2107 is not inserted (or fully inserted), then no pre-load is detected, and the electronics system provides a warning to the user.

In other embodiments, shear forces are measured to provide an indication of fluid pressure. A slide assembly 2207 is comprised of a support assembly 2202, piezoelectric shear sensors 2203, and a nose 2204 having a proximate nose wall 2204a and a sidewall 2204b, a shown in FIG. 20. A lead screw 2201 is secured to the support assembly 2202. The piezoelectric shear sensors 2203 are disposed between the support assembly 2202 and the sidewall 2204b of the nose 2204. A stopper 2205 is slidably mounted in a reservoir 2206. The stopper 2205 has a proximate wall 2209 and a generally cylindrical sidewall 2210 that form a cavity 2208 adapted to receive the nose 2204 portion of the slide assembly 2207. However, in alternative embodiments, the stopper 2205 does not have a cavity. Rather, the nose 2204 abuts the distal wall 2210 of the stopper 2205.

Returning to FIG. 20, as the lead screw 2201 advances, the support assembly 2202 and nose 2204 move axially to engage the stopper 2205, and then move the stopper 2205 into the reservoir 2206, forcing fluid from the reservoir 2206.

The force required to move the stopper 2205 is measured as shear forces placed on the piezoelectric shear sensors 2203. As the pressure on the stopper 2205 increases, the shear forces between the nose 2204 and the support assembly 2202 increase and apply shear force to the sensors 2203.

The previously described embodiments generally measure fluid pressure or forces exerted in an axial direction down the drive train. Alternative embodiments of the present invention however, measure a torque applied to a drive system component as an indication of the fluid pressure within a reservoir.

Figure 21:
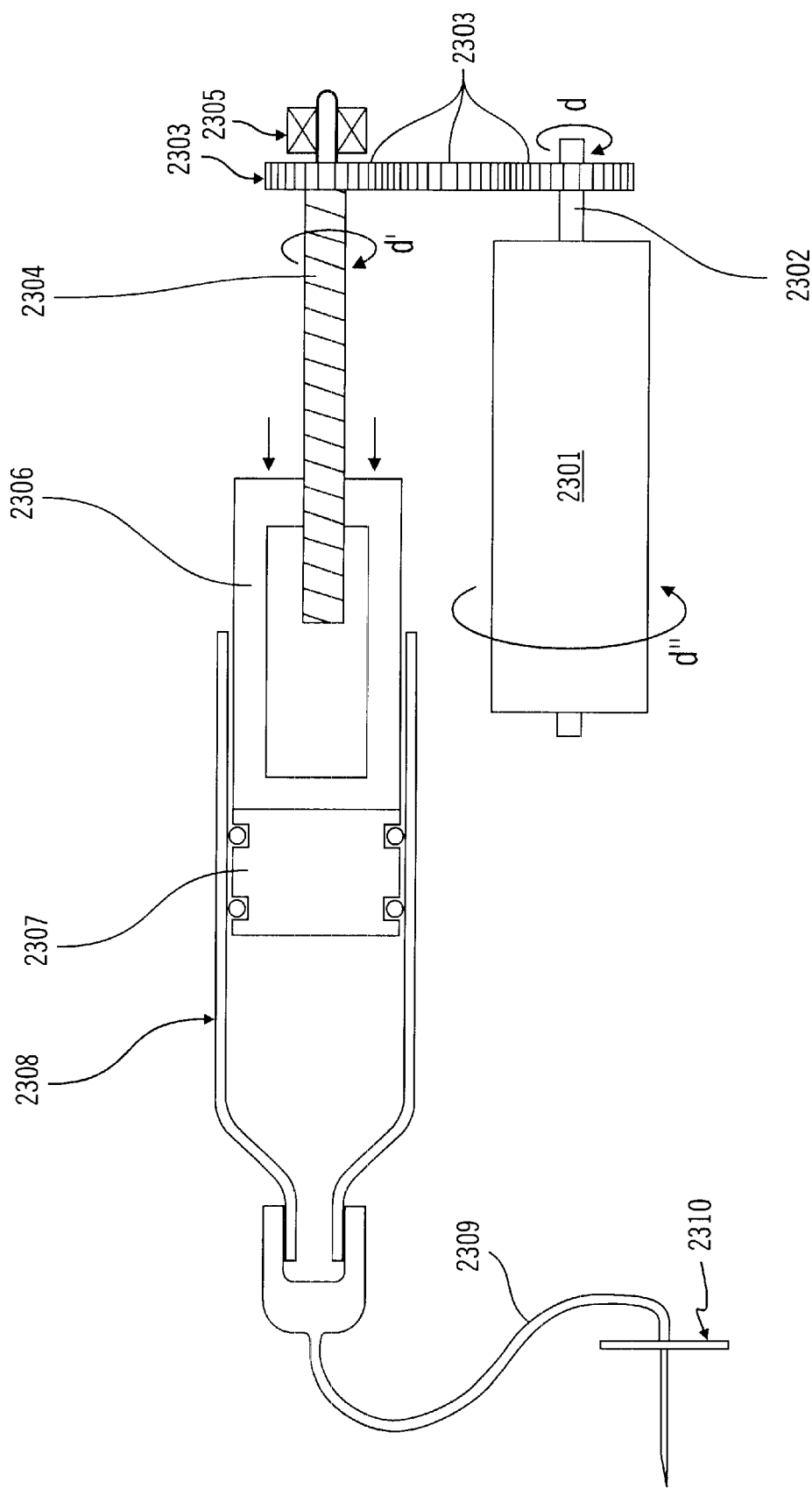
FIG. 21 is an illustration view of the infusion pump drive system of FIG. 4 showing certain torque forces.

In particular embodiments, a motor 2301 (or a motor with an attached gear box) has a drive shaft 2302 engaged to drive a set of gears 2303. The motor 2301 generates a torque powering the drive shaft 2302 in direction d, as shown in FIG. 21. The drive shaft 2302 rotates the gears 2303 to transfer the torque to a lead screw 2304, rotating the lead screw 2304 in the direction d'. The lead screw 2304 is mounted on a bearing 2305 for support. The threads of the lead screw 2304 are engaged with threads (not shown) in a slide 2306. The slide 2306 is engaged with a slot (not shown) in the housing (not shown) to prevent the slide 2306 from rotating, but allowing it to translate along the length of the lead screw 2304. Thus, the torque d' of the lead screw 2304 is transferred to the slide 2306 causing the slide 2306 to move in an axial direction, generally parallel to the drive shaft 2302 of the motor 2301. The slide 2306 is in contact with a stopper 2307 inside a reservoir 2308. As the slide 2306 advances, the stopper 2307 is forced to travel in an axial direction inside the reservoir 2308, forcing fluid from the reservoir 2308, through tubing 2309, and into an infusion set 2310.

Should an occlusion arise, the stopper 2307 is forced to advance, and pressure in the reservoir 2308 increases. The force of the stopper 2307 pushing against the fluid results in a reaction torque d" acting on the motor $2\square_1$. In particular embodiments, sensors are used to measure the torque d" applied to the motor 2301, and the sensor measurement is used to estimate the pressure in the reservoir 2308.

Figure 22A:
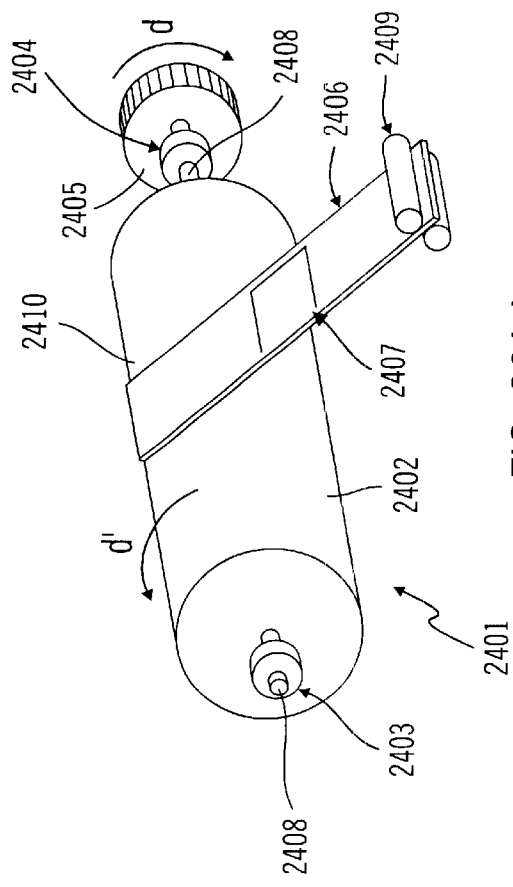
FIG. 22(a) is a perspective view of a sensor in a portion of a drive system according to a twenty-first embodiment of the present invention.
Figure 22B:
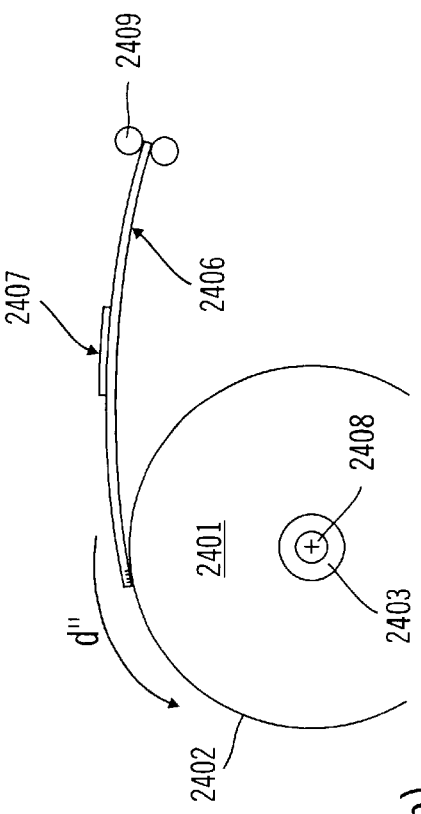
FIG. 22(b) is a rear view of the sensor and pump drive system of FIG. 22(a).

In particular embodiments, a motor 2401 has a motor case 2402, a proximate bearing 2403, a distal bearing 2404, a motor shaft 2408, and a gear 2405, as shown in FIGS. 22(a and b). The motor 2401 is secured to a housing (not shown)

or other fixed point by a beam 2406. One end of the beam 2406 is secured to the motor case 2402 at an anchor point 2410, and the other end of the beam 2406 is secured to the housing (not shown) at a housing anchor point 2409. A strain gauge sensor 2407 is mounted on the beam 2406.

Each end of the motor shaft 2408 is mounted on the bearings 2403 and 2404 that provide axial support but allow the motor shaft 2408 and motor 2401 to rotate. The beam 2406 supplies a counter moment in the direction d' that is equal in magnitude and opposite in direction to the motor driving torque d. As the torque produced by the motor 2401 increases, the reaction moment d" in the beam 2406 increases thereby increasing the strain within the beam 2406 and causing the beam 2406 to deflect. The strain gauge sensor 2407 mounted on the beam 2406 is used to measure deflection of the beam 2406. The electronics system (not shown) converts the strain gauge sensor measurements to estimates of fluid pressure in a reservoir (not shown) or force acting on the drive train (not shown).

This method of measurement provides information about the pressure within the reservoir (and frictional stack-up), as well as information about the drive train. If for example, there were a failure within the drive train such as, in the gearing, bearings, or lead screw interface, the torque measured at the strain gauge sensor 2407 would detect the failure. In further embodiments, the strain gauge 2407 is used to confirm motor activation and fluid delivery. During normal fluid delivery, the measured moment increases shortly while the motor is activated, and then decreases as fluid exits the reservoir relieving pressure and therefore the moment. The electronics system is programmed to confirm that the measured moment increases during motor activation and that the moment decreases back to a resting state after the motor is no longer powered In still further embodiments, a beam provides the necessary compliance to protect a drive system from a rewind hard stop. A motor is used to rewind a slide in preparation to replace a reservoir. However, once the slide is fully retracted, a hard stop at full motor speed could damage or reduce the life of drive system components. The beam absorbs the energy when the slide reaches the fully retracted position, without damaging the drive system.

A strain gauge sensor can work in several modes common to strain gauge sensor technology. For example, the strain gauge sensor could be mounted such that it measures tension or compression, or bending. In addition, a strain gauge sensor could be mounted to compensate for temperature variances and other system noises. Furthermore, the designs of FIGS. 19–22(b) are not limited to strain gauge sensor technology. Piezoelectric, capacitive, or magnetic sensors could be used as well.

Figure 23:
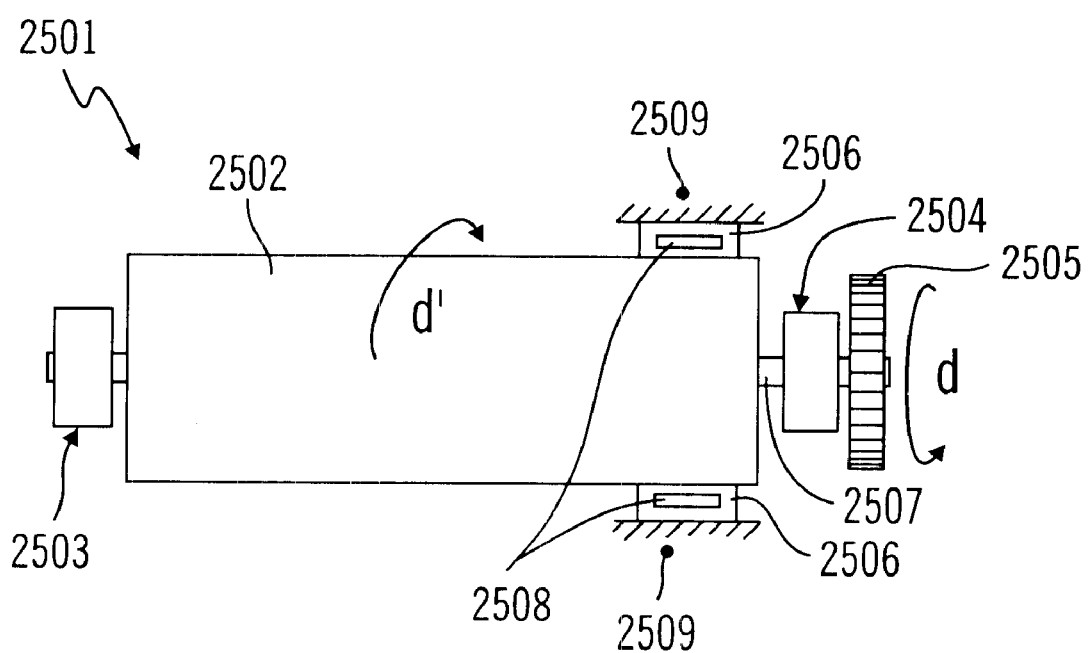
FIG. 23 is an illustration view of a sensor in a portion of a pump drive system according to a twenty-second embodiment of the present invention.

In alternative embodiments, a motor 2501 has a case 2502, a proximate bearing 2503, a distal bearing 2504, a motor shaft 2507, and a gear 2505, as shown in FIG. 23. The portion of the drive train not shown in FIG. 23 is similar to that shown in FIG. 21. The proximate bearing 2503 is disposed on one side of the pump motor 2501, and the distal bearing 2504 is disposed on the opposite side of the pump motor 2501. Motor mounts 2506 secure the case 2502 to the housing 2509 (or other fixed point). Piezoelectric shear mode sensors 2508 are secured to the mounts 2506. As the reaction torque d' increases due to an increase in the applied drive torque d, shear stress in the motor mounts 2506 increase. The sensors 2508 in turn provide a voltage correlated to the drive torque d. As discussed previously, the drive torque d is correlated to the fluid pressure in a reservoir (not shown).

Although the pump drive systems described above incorporate the placement of sensors at certain locations on pump drive trains, alternative embodiments of the present invention include sensors, which are coupled to any dynamic drive train component, in order to measure fluid pressure in a pump drive system.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An occlusion detection system for detecting an occlusion in a fluid path of an infusion pump with a reservoir containing fluid for delivering fluid to a user, the occlusion detection system comprising:

a housing;

a motor contained within the housing;

one or more drive train components that react to stimulus from the motor to force a fluid from a reservoir into the user;

a sensor positioned between the motor and a housing component to measure a parameter associated with the motor or a drive train component, wherein one or more components including the sensor are stacked between the motor and the housing component, and wherein the housing component is positioned to remove space between the one or more components before the housing component is attached to the housing, wherein the sensor produces three or more output levels across a range of measurements; and an electronics system that processes the three or more output levels to declare when an occlusion exists.

2. An occlusion detection system according to claim 1, wherein the sensor measures a force proportional to a force applied to a drive train component.

3. An occlusion detection system according to claim 2, wherein the drive train component is a lead screw.

4. An occlusion detection system according to claim 2, wherein the drive train component is a slide.

5. An occlusion detection system according to claim 1, wherein the sensor is a force sensitive resistor.

6. An occlusion detection system according to claim 1, wherein the sensor is a capacitive sensor.

7. An occlusion detection system according to claim 1, wherein the sensor is a strain gauge.

8. An occlusion detection system according to claim 1, wherein the sensor is a piezoelectric sensor.

9. An occlusion detection system according to claim 1, wherein the electronics system uses a maximum measurement threshold method to declare when an occlusion exists.

10. An occlusion detection system according to claim 9, wherein a measurement threshold is at least 2.00 pounds.

11. An occlusion detection system according to claim 1, wherein the electronics system uses a slope threshold method to declare when an occlusion exists.

12. An occlusion detection system according to claim 11, wherein a slope threshold is about 0.05 pounds per measurement.

13. An occlusion detection system according to claim 1, wherein the electronics system uses a maximum measurement threshold method, and a slope threshold method to declare when an occlusion exists.

14. An occlusion detection system according to claim 1, wherein one or more measurements must exceed a minimum level to declare that an occlusion exists.

15. An occlusion detection system according to claim 1, wherein the measured parameter is correlated with a fluid pressure in the reservoir.

16. An occlusion detection system according to claim 1, wherein VHB adhesive is positioned between the motor and the housing component.

17. An occlusion detection system according to claim 1, wherein the sensor is a multi-switch sensor.

18. An occlusion detection system for detecting an occlusion in a fluid path of an infusion pump with a reservoir containing fluid for delivering fluid to a user, the occlusion detection system comprising:
 a housing;
 a motor contained within the housing;
 one or more drive train components that react to stimulus from the motor to force a fluid from a reservoir into the user;
 a sensor positioned to measure a parameter associated with the motor or a drive train component,
 wherein the sensor measures tension or compression on a beam proportional to a torque applied to the motor, and wherein the sensor produces three or more output levels across a range of measurements; and
 an electronics system that processes the three or more output levels to declare when an occlusion exits.

19. An occlusion detection system according to claim 18, wherein the drive train component is a beam.

20. An occlusion detection system according to claim 18, wherein the drive train component is one or more mounts.

21. An occlusion detection system for detecting an occlusion in a fluid path of an infusion pump with a reservoir containing fluid for delivering fluid to a user, the occlusion detection system comprising:
 a housing;
 a motor contained within the housing;
 one or more drive train components that react to stimulus from the motor to force a fluid from a reservoir into the user;
 a sensor positioned to measure a parameter associated with the motor or a drive train component,
 wherein the sensor measures tension or compression proportional to a pressure applied to a drive train component, and wherein the sensor produces three or more output levels across a range of measurements; and
 an electronics system that processes the three or more output levels to declare when an occlusion exists.

22. An occlusion detection system according to claim 21, wherein the drive train component is a bellows.

23. An occlusion detection system according to claim 21, wherein the drive train component is a cap.

24. An occlusion detection system for detecting an occlusion in a fluid path of an infusion pump with a reservoir containing fluid for delivering fluid to a user, the occlusion detection system comprising:
 a housing;
 a motor contained within the housing;
 one or more drive train components that react to stimulus from the motor to force a fluid from a reservoir into the user;
 a sensor positioned to measure a parameter associated with the motor or a drive train component,
 wherein the sensor produces three or more output levels across a range of measurements; and
 an electronics system that processes the three or more output levels to declare when an occlusion exits, wherein the electronics system processes the sensor output levels to determine when the reservoir is empty.

25. An occlusion detection system for detecting an occlusion in a fluid path of an infusion pump with a reservoir containing fluid for delivering fluid to a user, the occlusion detection system comprising:
 a housing;
 a motor contained within the housing;
 one or more drive train components that react to stimulus from the motor to force a fluid from a reservoir into the user;
 a sensor positioned to measure a parameter associated with the motor or a drive train component,
 wherein the sensor produces three or more output levels across a range of measurements; and
 an electronics system that processes the three or more output levels to declare when an occlusion exists, wherein the electronics system processes the sensor output levels to determine when a stopper contacts an end of the reservoir.

26. An occlusion detection system for detecting an occlusion in a fluid path of an infusion pump with a reservoir containing fluid for delivering fluid to a user, the occlusion detection system comprising:
 a housing;
 a motor contained within the housing;
 one or more drive train components that react to stimulus from the motor to force a fluid from a reservoir into the user;
 a sensor positioned to measure a parameter associated with the motor or a drive train component,
 wherein the sensor produces three or more output levels across a range of measurements; and
 an electronics system that processes the three or more output level to declare when an occlusion exists, wherein the electronics system processes the sensor output levels to determine when a slide is seated in a stopper.

27. An occlusion detection system for detecting an occlusion in a fluid path of an infusion pump with a reservoir containing fluid for delivering fluid to a user, the occlusion detection system comprising:
 a housing;
 a motor contained within the housing;
 one or more drive train components that react to stimulus from the motor to force a fluid from a reservoir into the user;
 a sensor positioned to measure a parameter associated with the motor or a drive train component, wherein one or more components including the sensor are stacked between the motor and the housing, and wherein backfill material is injected through the housing to remove space between the one or more components and to fill the space between the one or more components and the housing,
 wherein the sensor produces three or more output levels across a range of measurements; and
 an electronics system that processes the three or more output levels to declare when an occlusion exists.

28. A method of detecting an occlusion in an infusion pump for infusing fluid into the body of a user, the method comprising the steps of:
- obtaining a measurement from a sensor before each fluid delivery;
- calculating a current slope of a line using two or more measurements;
- calculating an average slope using a previous average slope and the current slope;
- comparing the average slope to a slope threshold;
- incrementing a counter when the average slope exceeds the slope threshold;
- declaring an occlusion when the counter exceeds a detection count.

29. The method according to claim 28, wherein the two or more measurements are not consecutive.

30. The method according to claim 28, further comprising the step of restarting the counter when the average slope is below the slope threshold.

31. An occlusion detection system for detecting an occlusion in a fluid path of an infusion pump with a reservoir for containing fluid for delivering fluid to a user, the occlusion detection system comprising:
- a housing;
- forcing means for forcing fluid from a reservoir containing a fluid;
- sensing means for sensing a parameter associated with the forcing means for forcing fluid from the reservoir to obtain one or more measurements;
- wherein one or more components including the sensing means are stacked between the forcing means and a housing component, and wherein the housing component is positioned to remove space between the one or more components before the housing component is attached to the housing,
- wherein the sensing means produces one of three or more output levels for each of the one or more the measurements; and
- evaluation means for evaluating the one of three or more output levels associated with each of the one or more measurements to declare when an occlusion exists.

* * * * *